US011001816B2

(12) United States Patent
Klausing et al.

(10) Patent No.: US 11,001,816 B2
(45) Date of Patent: May 11, 2021

(54) POLYMERASES, COMPOSITIONS, AND METHODS OF USE

(71) Applicants: Illumina, Inc., San Diego, CA (US); Illumina Cambridge Limited, Cambridge (GB); Illumina Singapore Pte. Ltd., Singapore (SG)

(72) Inventors: Kay Klausing, San Diego, CA (US); Hamed Tabatabaei Ghomi, Cambridge (GB); Misha Golynskiy, San Diego, CA (US); Saurabh Nirantar, Singapore (SG); Seth McDonald, San Diego, CA (US); Sergio Peisajovich, San Diego, CA (US)

(73) Assignees: Illumina, Inc., San Diego, CA (US); Illumina Singapore PTE. LTD., Singapore (SG); Illumina Cambridge Limited, Cambridge (GB)

( * ) Notice: Subject to any disclaimer, the term of this patent is extended or adjusted under 35 U.S.C. 154(b) by 0 days.

(21) Appl. No.: 16/703,569

(22) Filed: Dec. 4, 2019

(65) Prior Publication Data
US 2020/0181587 A1 Jun. 11, 2020

Related U.S. Application Data

(60) Provisional application No. 62/775,662, filed on Dec. 5, 2018.

(51) Int. Cl.
*C12N 9/12* (2006.01)

(52) U.S. Cl.
CPC .... *C12N 9/1252* (2013.01); *C12Y 207/07007* (2013.01)

(58) Field of Classification Search
CPC .................................................. C12N 9/1252
See application file for complete search history.

(56) References Cited

U.S. PATENT DOCUMENTS

| | | | |
|---|---|---|---|
| 5,882,904 A | 3/1999 | Riedl et al. | |
| 5,948,666 A | 9/1999 | Callen et al. | |
| 6,333,183 B1 | 12/2001 | Evans et al. | |
| 6,492,161 B1 | 12/2002 | Hjorleifsdottir et al. | |
| 7,892,797 B2 | 2/2011 | Mitsis et al. | |
| 8,268,605 B2 | 9/2012 | Sorge | |
| 8,460,910 B2 | 6/2013 | Smith et al. | |
| 8,623,628 B2 | 1/2014 | Ost et al. | |
| 8,852,910 B2 | 10/2014 | Smith et al. | |
| 9,273,352 B2 | 3/2016 | Smith et al. | |
| 9,447,389 B2 | 9/2016 | Smith et al. | |
| 9,447,445 B2 * | 9/2016 | Hsieh ....................... | C12N 9/96 |
| 9,677,057 B2 | 6/2017 | Bomati et al. | |
| 9,765,309 B2 | 9/2017 | Chen et al. | |
| 10,017,750 B2 | 7/2018 | Smith et al. | |
| 10,059,928 B2 | 8/2018 | Smith et al. | |
| 10,150,954 B2 | 12/2018 | Bomati et al. | |
| 10,421,996 B2 | 9/2019 | Bomati et al. | |
| 10,696,955 B2 | 6/2020 | Bomati et al. | |
| 10,745,751 B2 | 8/2020 | Bomati et al. | |
| 2002/0132249 A1 | 9/2002 | Patel et al. | |
| 2003/0228616 A1 | 12/2003 | Arezi et al. | |
| 2005/0069908 A1 | 3/2005 | Sorge et al. | |
| 2006/0240439 A1 | 10/2006 | Smith et al. | |
| 2006/0281109 A1 | 12/2006 | Barr Ost et al. | |
| 2007/0048748 A1 | 3/2007 | Williams et al. | |
| 2011/0269211 A1 | 11/2011 | Bourn et al. | |
| 2011/0301041 A1 | 12/2011 | Davidson et al. | |
| 2012/0020537 A1 | 1/2012 | Garcia et al. | |
| 2012/0094296 A1 | 4/2012 | Tabata et al. | |
| 2014/0296082 A1 | 10/2014 | Gardner | |
| 2015/0024463 A1 | 1/2015 | Smith et al. | |
| 2015/0376582 A1 | 12/2015 | Chen et al. | |
| 2016/0032377 A1 | 2/2016 | Chen et al. | |
| 2016/0090579 A1 | 3/2016 | Bomati et al. | |
| 2016/0115461 A1 | 4/2016 | Smith et al. | |
| 2017/0275602 A1 * | 9/2017 | Smith ..................... | C12Q 1/686 |
| 2017/0355970 A1 | 12/2017 | Chen et al. | |
| 2018/0119115 A1 | 5/2018 | Lin Wu et al. | |
| 2018/0298358 A1 | 10/2018 | Smith et al. | |
| 2019/0330602 A1 | 10/2019 | Wang et al. | |
| 2020/0002689 A1 | 1/2020 | Olejnik et al. | |
| 2020/0080065 A1 | 3/2020 | Fuller et al. | |
| 2020/0087637 A1 | 3/2020 | Iyidogan | |
| 2020/0087638 A1 | 3/2020 | Iyidogan | |
| 2020/0117968 A1 | 4/2020 | Ulyate | |
| 2020/0131484 A1 | 4/2020 | Golynskiy et al. | |

(Continued)

FOREIGN PATENT DOCUMENTS

| | | | |
|---|---|---|---|
| AU | 2007/201277 A1 | 8/2007 | |
| EP | 0701000 A3 | 3/1996 | |
| EP | 0822256 A2 | 2/1998 | |

(Continued)

OTHER PUBLICATIONS

Rodriguez et al., "Crystal Structure of a Pol alpha Family DNA Polymerase from the Hyperthermophilic Archaeon *Thermococcus* sp. 9oN-7", J. Mol. Biol., 2000, vol. 299, pp. 447-462.*
International Search Report for PCT/US2019/064524, PCT 210. Published Jul. 10, 2020.*
Gardner and Kelman, et al., "DNA polymerases in biotechnology", Frontiers in Microbiology, Jan. 1, 2015, 1-3.
Hashimoto, et al., "Crystal Structure of DNA Polymerase from Hyperthermophilic Archaeon Pyrococcus codakaraensis KOD1", J. Mol. Biol, 306, 2001, 469-77.
Laos, R., et al., "DNA polymerases engineered by directed evolution to incorporate non-standard nucleotides", Frontiers in Microbiology, Oct. 31, 2014, 1-14.

(Continued)

*Primary Examiner* — Suzanne M Noakes
(74) *Attorney, Agent, or Firm* — Mueting Raasch Group

(57) ABSTRACT

Presented herein are altered polymerase enzymes for improved incorporation of nucleotides and nucleotide analogues, in particular altered polymerases that maintain high fidelity under reduced incorporation times, as well as methods and kits using the same.

30 Claims, 7 Drawing Sheets
Specification includes a Sequence Listing.

(56) References Cited

U.S. PATENT DOCUMENTS

| | | |
|---|---|---|
| 2020/0181587 A1 | 6/2020 | Klausing et al. |
| 2020/0231947 A1 | 7/2020 | Piest et al. |

FOREIGN PATENT DOCUMENTS

| | | |
|---|---|---|
| EP | 0892058 A2 | 1/1999 |
| EP | 0701000 B1 | 1/2001 |
| EP | 1208230 B1 | 11/2005 |
| WO | WO 91/06678 A1 | 5/1991 |
| WO | WO 97/39150 A1 | 10/1997 |
| WO | WO 01/23411 A2 | 4/2001 |
| WO | WO 01/32887 A1 | 5/2001 |
| WO | WO 02/101358 A2 | 12/2002 |
| WO | WO 03/048387 A2 | 6/2003 |
| WO | WO 03/054139 A2 | 7/2003 |
| WO | WO 2004/018497 A2 | 3/2004 |
| WO | WO 2004/039947 A2 | 5/2004 |
| WO | WO 2005/024010 A1 | 3/2005 |
| WO | 2006/037064 A2 | 4/2006 |
| WO | WO 2006/037064 A2 | 4/2006 |
| WO | WO 2006/120433 A1 | 11/2006 |
| WO | WO 2007/076057 A2 | 7/2007 |
| WO | WO 2007/123744 A2 | 11/2007 |
| WO | WO 2008/029084 A1 | 3/2008 |
| WO | WO 2008/029085 A2 | 3/2008 |
| WO | WO 2008/051530 A2 | 5/2008 |
| WO | WO 2008/083393 A2 | 7/2008 |
| WO | WO 2009/131919 A2 | 10/2009 |
| WO | WO 2011/026194 A1 | 3/2011 |
| WO | WO 2011/135280 A2 | 3/2011 |
| WO | WO 2012/058096 A1 | 5/2012 |
| WO | WO 2012/154934 A1 | 11/2012 |
| WO | WO 2014/142921 A1 | 9/2014 |
| WO | WO 2015/200693 A1 | 12/2015 |
| WO | 2016/033315 A2 | 3/2016 |
| WO | WO 2016/033315 A2 | 3/2016 |
| WO | WO 2016/054096 A1 | 4/2016 |
| WO | WO 2017/042040 A1 | 3/2017 |
| WO | WO 2018/126470 A1 | 7/2018 |
| WO | WO 2018/148723 A1 | 8/2018 |
| WO | WO 2018/148724 A1 | 8/2018 |
| WO | WO 2018/148726 A1 | 8/2018 |
| WO | WO 2018/148727 A1 | 8/2018 |
| WO | WO 2020/048329 A1 | 3/2020 |
| WO | WO 2020/056044 A1 | 3/2020 |
| WO | WO 2020/060811 A1 | 3/2020 |
| WO | 2020/092830 A1 | 5/2020 |
| WO | WO 2020/092830 A1 | 5/2020 |
| WO | 2020117968 A2 | 6/2020 |

OTHER PUBLICATIONS

Alignments, Result 1 US-15-688-473-95, U.S. Appl. No. 15/688,473 Sequence 95; Result 2 US-15-632-733-25, U.S. Appl. No. 15/632,733 Sequence 25; 4 pages.

Arezi et al., "Efficient and High Fidelity Incorporation of Dye-terminators by a Novel Archaeal DNA Polymerase Mutant," *J. Mol. Biol*, Sep. 2002; 322(4):719-729.

Banerjee et al., "Improving enzymes for biomass conversion: A basic research perspective," *Bioenerg. Res.*, 2010; 3:82-92.

Bonnin et al., "A Single Tyrosine Prevents Insertion of Ribonucleotides in the Eukaryotic-type φ29 DNA Polymerase," *J. Mol. Biol.* Jul. 1999; 290(1):241-251.

Branden et al., "Introduction to Protein Structure", Garland Publishing Inc., New York, 1991;p. 247.

Broun et al., "Catalytic plasticity of fatty acid modification enzymes underlying chemical diversity of plant lipids," *Science*, 1998; 282:1315-1317.

Canard et al., "DNA polymerase fluorescent substrates with reversible 3'-tags," *Gene*, Oct. 1994; 148(1):1-6.

Chen, "DNA polymerases drive DNA sequencing by-synthesis technologies: both past and present," *Frontiers in Microbiology*, Jun. 24, 2014; vol. 5: 12 pgs.

Chica et al., "Semi-rational approaches to engineering enzyme activity: combining the benefits of directed evolution and rational design," *Curr. Opi. Biotech*, Aug. 2005;616(4):378-384.

Cooper et al., "Chapter 2: The Composition of Cells," in *The Cell: A Molecular Approach, Fourth Edition*. ASM Press (Ed). Sinauer Associates, Inc.: Sunderland, MA; 2007. Cover page, publisher's page, and pp. 52-53.

Database UniProt [Online], "RecName: Full=DNA polymerase; EC=2.7.7.7; AltName:Full=Pwo polymerase; EGKVITRGLE IVRRDWSEIA KETQARVLET ILKHGDVEEA VRIVEVIQK LANYEIPPEK", XP002746834, retrieved from EBI accession No. UNIPORT:P61876, Database accession No. P61876, Jun. 7, 2004.

Database UniProt [Online], RecName: Full=DNA polymerase {EC0:00002561 RuleBase:RU000442}; EC=2.7.7.7 {EC0:00002561 RuleBase:RU000442}; XP002746835, retrieved from EBI accession No. UNIPORT:A8AACO Database accession No. A8AACO; sequence, Oct. 23, 2007.

Devos et al., "Practical limits of functional prediction," *Proteins: Structure, Function and Genetics*, 2000; 41:98-107.

Dong et al., "Mutational Studies of Human DNA Polymerase alpha. Serine 867 in the second most conserved region among alpha-like DNA polymerases is involved in primer binding and mispair primer extension," *The Journal of Biological Chemistry*, Nov. 1993; 268(32):24175-24182.

Dong et al., "Mutational studies of human DNA polymerase alpha: Identification of residues critical for deoxynucleotide binding and misinsertion fidelity of DNA synthesis," *The Journal of Biological Chemistry*, Nov. 1993; 268(32):24163-24174.

Doublie et al., "Crystal structure of a bacteriophage T7 DNA replication complex at 2.2 Å resolution," *Nature*, Jan. 1998; 391:251-258.

Evans et al., "Improving dideoxynucleotide-triphosphate utilisation by the hyper-thermophilic DNA polymerase from the archaeon Pyrococcus furiosus", *Nucleic Acids Res.*, Mar. 2000; 2(5):1059-1066.

Franklin et al., "Structure of the Replicating Complex of a Pol α Family DNA Polymerase," *Cell*, Jun. 2001; 105(5):657-667.

Gardner et al., "Determinants of nucleotide sugar recognition in an archaeon DNA polymerase," *Nucleic Acids Res.*, Jun. 1999; 27(12):2545-2553.

Gardner et al., "Acrylic and dideoxy terminator preferences denote divergent sugar recognition by archaeon and Taq DNA polymerases," *Nucleic Acids Res.*, Jan. 2002; 30(2):605-613.

Gardner et al., "Rapid Incorporation Kinetics and Improved Fidelity of a Novel Class of 3'-OH Unblocked Reversible Terminators," *Nucleic Acids Research*, Aug. 1, 2012;40(15): 7404-7415.

Gardner et al., "DNA Polymerases in Biotechnology", *Frontiers in Microbiology*, Dec. 1, 2014; 5:1-146.

Griffiths, et al., "New High Fidelity Polymerases from Thermococcus Species," *Protein Expression and Purification*, Academic Press, San Diego, CA, vol. 52, No. 1, Jan. 8, 2007, 19-30.

Guo et al., "Protein tolerance to random amino acid change" Jun. 2004, *PNAS* 101(25):9205-9210.

Hopfner et al., "Crystal structure of a thermostable type B DNA polymerase from *Thermococcus gorgonarius*," Mar. 1999, *Proc. Natl. Acad. Sci. USA*; 96:3600-3605.

Joyce et al., "Function and Structure Relationships in DNA Polymerases," *Annu. Rev. Biochem.*, 1994; 63:777-822.

Joyce et al., "Techniques used to study the DNA polymerase reaction pathway," *Biochimica et Biophysica Acta (BBA)—Proteins & Proteomics, Elsevier, Netherlands*, May 1, 2010; 1804(5):1032-1040.

Kaushik et al., "Significant of the 0-helix residues of *Escherichia coli* DNA polymerase I in DNA synthesis: dynamics of the dNTP binding pocket," *Biochemistry, American Chemical Society, US*, Jun. 4, 1996; 35(22):7256-7266.

Kim et al., Database Accession # E9KLD9, integrated into UniProtKB/TrEMBL Apr. 5, 2011; 2 pages.

Kranaster et al., "Engineered DNA Polymerases in Biotechnology," *Chembiochem*, Sep. 22, 2019;11(15):2077-2084.

Laos et al., "DNA polymerases engineered by directed evolution to incorporate non-standard nucleotides," *Frontiers in Microbiology*, Oct. 31, 2014; 5(565): 14 pgs.

(56) References Cited

OTHER PUBLICATIONS

Lee et al., Database Accession # F4HMC2, integrated into UniProtKB/TrEMBL Jun. 28, 2011; 2 pages.

Liu et al., "Identification of Conserved Residues Contributing to the Activities of Adenovirus DNA Polymerase," *J. Virol.*, Dec. 2000; 74(24):11681-11689.

Loakes et al., "Evolving a Polymerase for Hydrophobic Base Analogues," *Journal of the American Chemical Society*, Oct. 21, 2009;131(41):14827-14837.

Lutz et al., "Recognition of a Non-standard Base Pair by thermostable DNA Polymerases," *Bioorganic & Medicinal Chemistry Letters*, Jun. 1998; 8(10):1149-1152.

Metzker et al., "Termination of DNA synthesis by novel 3'-modified-deoxyribonucleoside 5'-triphosphases," *Nucleic Acids Res.*, Oct. 1994; 22(20):4259-4267.

Minnick et al., "A thumb subdomain in mutant of the large fragment of *Escherichia coli* DNA polymerase I with reduced DNA binding affinity, processivity, and frameshift fidelity", *The Journal of Biological Chemistry*, 1998, Oxford GB 8(10)1149-1152.

Morrison et al., "Combinatorial alanine-scanning", *Current Opinion in Chemical Biology*, 2001, 5:302-307.

Ngo et al., "The Protein Folding Problem and Tertiary Structure Prediction", 1994, Merz et al (ed.), Birkhauser, Boston, MA, 433 and 492-495.

Pavlov et al., "In Vivo consequences of putative active site mutations in yeast DNA polymerase alpha, epsilon, delta, and zeta," *Genetics*, Sep. 2001; 159(1):47-64.

PCT Patent Application No. PCT/US2019/064524 filed Dec. 4, 2019 International Search Report/Written Opinion dated Jul. 10, 2020, 21 pages.

PCT Patent Application No. PCT/US2019/059246 filed Oct. 31, 2019 Partial International Search Report/Written Opinion dated Mar. 20, 2020, 32 pages.

Polesky et al., "Identification of Residues Critical for the Polymerase Activity of the Klenow Fragment of DNA Polymerase I from *Escherichia coli*," *J. Biol. Chem.*, 1990; 265:14579-14591.

Querellou et al., Database Accession # Q9HH06, integrated into UniProtKB/TrEMBL Feb. 20, 2007; 2 pages.

Rodriguez et al., "Crystal structure of a pol alpha family DNA polymerase from the hyperthermophilic archaeon *Thermococcus sp. 9°N-7* ", *Journal of Molecular Biology*; Jun. 2000; 299 ( 2 ) : 447-462.

Sadowski et al., "The sequence-structure relationship and protein function prediction," *Current Opinion in Structural Biology*, Jun. 2009; 19(3):357-362.

Seffernick et al., "Melamine deaminase and Atrazine chlorohydrolase: 98 percent identical but functionally different," *J. Bacteriol.*, 2001; 183(8):2405-2410.

Sen et al., "Developments in directed evolution for improving enzyme functions," *Appl. Biochem. Biotechnol.*, 2007; 143:212-223.

Sensen et al., "Probable DNA-directed DNA Polymerase," PIR accession No. S75407, 1997; 2 pgs.

Shinkai et al., "The Conserved Active Site Motif A of *Escherichia coli* DNA Polymerase 1 is Highly Mutable", *Journal of Biological Chemistry*, 2001;276(220):18836-18842.

Shinkai et al., "in Vivo Mutagenesis by *Escherichia coli* DNA Polymerase I",*J. Biol. Chem.*, Dec. 2001, 276(5):46759-46764.

Song et al., "An Amino Acid Residue in the Middle of the Fingers Subdomain is Involved in new DNA Polymerase Processivity: Enhanced Processivity of Engineered New DNA Polymerase and its PCR Application", *Protein Engineering Design and Selection*, Nov 2010; 23(141): 835-842.

Southworth et al., "Cloning of thermostable DNA polymerases from hyperthermophilic marine Archaea with emphasis on Thermococcus sp. 9 degrees N-7 and mutations affecting 3' -5' Exonuclease activity", *Proc. Natl. Acad. Sci. USA.*, May 1996; 93(11):5281-5285.

St. Clair et al., "3'-Azido-3"-Deoxythymidine Triphosphate as an Inhibitor and Substrate of Purified Human Immunodeficiency Virus Reverse Transcriptase", *Antimicrob. Agents Chemother.*, Dec. 1987; 31(12): 1972-1977.

Stachelhaus et al., "The specificity-conferring code of adenylation domains in nonribosomal peptide synthetases", *Chem. Biol.*, Aug. 1999; 6(8):493-505.

Steitz, "DNA Polymerases: Structural Diversity and Common Mechanisms," *J. Biol. Chem.*, Jun. 1999; 274(25):17395-17398.

Suzuki et al., "Random mutagenesis of Thermus aquaticus DNA polymerase I: Concordance of immutable sites in vivo with the crystal structure", *Proc. Natl. Acad. Sci.*, Sep. 1996; 93(18): 9670-9675.

Tomic-Canic et al., "A Simple Method for Site-Specific Mutagenesis that Leaves the Rest of the Template Unaltered," *Methods Mol. Biol.*, 1996; 57:259-267.

Truniger, et al., "Function of the C-terminus of o 29 DNA polymerase in DNA and terminal protein binding", *Nucleic Acids Research* 32 2004, 361-370.

Tunitskaya et al., "Structural-functional Analysis of Bacteriophage T7 RNA Polymerase", *Biochemistry (Mosc.)*, Oct. 2002; 67(10):1124-1135.

Uniprot-Acension—https://www.uniprot.org/uniprot/Ps75/P61875.txt?version+65 printed Aug. 31, 2018, 4 pages.

UniProt [Online] Database; XP002775655; UNIPROT: Q9HH06; Feb. 20, 2007.

UniProt [Online] Database; XP002775656, UNIPROT: Q52415; Nov. 1, 1996.

Vanhercki et al., "Reducing mutational bias in random protein libraries" Dec 2005, *Analytical Biochemistry* 339:9-14.

Wang et al., "Human DNA polymerase alpha: predicted functional domains and relationships with viral DNA polymerases," *FASEB J.*, 1989; 3:14-21.

Welch et al., "Syntheses of Nucleosides Designed for Combinatorial DNA Sequencing", *Chemistry, European Journal*, Mar. 1999; 5(3): 951-960.

Whisstock et al., "Prediction of protein function from protein sequence," *Q. Rev. Biophysics.*, 2003; 36(3):307-340.

Witkowski et al., "Conversion of b-ketoacyl synthase to a Malonyl Decarboxylase by replacement of the active cysteine with glutamine," *Biochemistry*, 1999; 38:11643-11650.

Yang et al., "Steady-State Kinetic Characterization of RB69 DNA Polymerase Mutants That Affect dNTP Incorporation," *Biochemistry*, Jun. 1999, 38(25):8094-8101.

Yang et al., "A conserved Tyr residue is required for sugar selectivity in a Pol alpha DNA polymerase", *Biochemistry*, Aug. 2002; 41(32):10256-10261.

\* cited by examiner

FIG. 1

| | | |
|---|---|---|
| SEQ ID NO:1 | MILDTDYITENGKPVIRVFKKENGEFKIEYDRTFEPYFYALLKDDSAIEDVKKVTAKRHG | 60 |
| SEQ ID NO:2 | MILDTDYITKDGKPIIRIFKKENGEFKIELDPHFQPYIYALLKDDSAIEEIKAIKGERHG | 60 |
| SEQ ID NO:7 | MILDADYITEDGKPVIRVFKKEKGEFKINYDRDFEPYIYALLKDDSAIEDIKKITAERHG | 60 |
| SEQ ID NO:5 | MILDTDYITEDGKPVIRIFKKENGEFKIEYDRTFEPYFYALLKDDSAIEEVKKITAERHG | 60 |
| SEQ ID NO:4 | MILDVDYITEEGKPVIRLFKKENGKFKIEHDRTFRPYIYALLRDDSKIEEVKKITGERHG | 60 |
| SEQ ID NO:3 | MILDADYITEDGKPIIRIFKKENGEFKVEYDRNFRPYIYALLKDDSQIDEVRKITAERHG | 60 |
| SEQ ID NO:6 | MILDADYITEDGKPIIRIFKKEKGEFKVEYDRTFRPYIYALLKDDSAIDEVKKITAERHG | 60 |
| | *::*:****::*:*:***:::: *.:**:*:*:*.* .::: .:*** | |
| SEQ ID NO:1 | TVVKVKRAEKVQKKFLGRPIEVWKLYFNHPQDVPAIRDRIRAHPAVVDIYEYDIPFAKRY | 120 |
| SEQ ID NO:2 | KTVRVLDAVKVKRKFLGREVEVWKLIFEHPQDVPAMRGKIREHPAVVDIYEYDIPFFAKRY | 120 |
| SEQ ID NO:7 | TTVRVTRAERVKKKFLGRPVEVWKLYFTHPQDVPAIRDKIREHPAVVDIYEYDIPFAKRY | 120 |
| SEQ ID NO:5 | TVVTVKRVERVQKKFLGRPVEVWKLYFTHPQDVPAIRDKIREHPAVIDIYEYDIPFAKRY | 120 |
| SEQ ID NO:4 | KIVRIVDVEKVEKKFLGKPITVWKLYLEHPQDVPTIREKVREHPAVVDIFEYDIPFAKRY | 120 |
| SEQ ID NO:3 | KIVRIIDAEKVRKKFLGRPIEVWKLYFEHPQDVPAIRDKIREHSAVIDIFEYDIPFAKRY | 120 |
| SEQ ID NO:6 | KIVRITEVEKVQKKFLGRPIEVWKLYLEHPQDVPAIREKIREHPAVVDIFEYDIPFAKRY | 120 |
| | . :: *.:*::** :**:*. :****:*.:*::*:.:.*:::*:* | |
| SEQ ID NO:1 | LIDKGLIPMEGDEELTMLAFDIETLYHEGEEFGTGPILMISYADGSEARVITWKKIDLPY | 180 |
| SEQ ID NO:2 | LIDKGLIPMEGDEELKLLAFDIATFYHEGDEFGKGEIIMISYADEEEARVITWKNIDLPY | 180 |
| SEQ ID NO:7 | LIDKGLIPMEGNEELRMLAFDIETLYHEGEEFGEGPILMISYADEEGARVITWKNVDLPY | 180 |
| SEQ ID NO:5 | LIDKGLVPMEGDEELKMLAFAIATLYHEGEEFAEGPILMISYADEEGARVITWKNVDLPY | 180 |
| SEQ ID NO:4 | LIDKGLIPMEGEEELKILAFDIETLYHEGEEFGKGPIIMISYADENEAKVITWKNIDLPY | 180 |
| SEQ ID NO:3 | LIDKGLIPMEGDEELKLLAFAIATFYHEGEEFAKGPIIMISYADEEEAKVITWKKIDLPY | 180 |
| SEQ ID NO:6 | LIDKGLTPMEGNEELTFLAVAIATLYHEGEEFGKGPIIMISYADEEGAKVITWKSIDLPY | 180 |
| | **** .* :**. *:.*****:*. * *:**:: :.:*. ** | |

FIG. 1 cont'd

```
SEQ ID NO:1  VDVVSTEKEMIKRFLRVVREKDPDVLITYNGDNEFDFAYLKKRCEELGIKFTLGRDG--SE  238
SEQ ID NO:2  VDVVSNEREMIKRFVQVVKEKDPDVLITYNGDNFDLPYLIKRAEKLGVRLVLGRDKEHPE  240
SEQ ID NO:7  VESVSTEKEMIKRFLKVIQEKDPDVLITYNGDNEFDFAYLKKRSETLGVKFTLGRDG--SE  238
SEQ ID NO:5  VDVVSTEREMIKRFLRVVKEKDFDVLITYNGDNEFDFAYLKKRCEKLGINFALGRDG--SE  238
SEQ ID NO:4  VEVVSSEREMIKRFLRIIREKDPDIIVTYNGDSFDFPYLAKRAEKLGIKLTIGRDG--SE  238
SEQ ID NO:3  VEVVSSEREMIKRFLKVIREKDFDVITYNGDSFDLPYLVKRAEKLGIKIPLGRDG--SE  238
SEQ ID NO:6  VEVVSSEREMIKRLVKVIREKDPDVITYNGDNEFDFPYLLKRAEKLGIKLPLGRDN--SE  238
             *: .* :.***:***: :*:: ***.*:.**:*:* :.:***:*** :: *:**.  *

SEQ ID NO:1  PKIQRMGDRFAVEVKGRIHFDLYPVIRRTINLPTYTLEAVYEAVFGKPKEKVYAEEIAQA  298
SEQ ID NO:2  PKIQRMGDSFAVEIKGRIHFDLFPVVRRTINLPTYTLEAVYEAVLGKTKSKLGAEEIAAI  300
SEQ ID NO:7  PKIQRMGDRFAVEVKGRIHFDLYPVIRRTINLPTYTLETVYEAIFGQPKEKVYAEEIAQA  298
SEQ ID NO:5  PKIQRMGDRFEAVEVKGRIHFDLYPVIRRTINLPTYTLEAVYEAVFGQPKEKVYAEEITTA  298
SEQ ID NO:4  PKMQRIGDMTAVEVKGRIHFDLYHVIRRTINLPTYTLEAVYEAIFGKPKEKVYADEIAKA  298
SEQ ID NO:3  PKMQRLGDMTAVEIKGRIHFDLYHVIRRTINLPTYTLEAVYEAIFGKPKEKVYAHEIAEA  298
SEQ ID NO:6  PKMQRMGDSLAVEIKGRIHFDLFPVIRRTINLPTYTLEAVYEAIFGKSKEKVYAHEIAEA  298
             **:**:**  **:******: *::************.***::*:  **:*:.*

SEQ ID NO:1  WESGEGLERVARYSMEDAKVTYELGREFFPMEAQLSRLIGQSIWDVSRSSTGNLVEWFLL  358
SEQ ID NO:2  WETEESMKKLAQYSMEDARATYELGKEFFPMEAELAKLIGQSVWDVSRSSTGNLVEWYLL  360
SEQ ID NO:7  WESGEGLERVARYSMEDAKATYELGKEFFPMEAQLSRLIGQSLWDVSRSSTGNLVEWFLL  358
SEQ ID NO:5  WETGENLERVARYSMEDAKVTYELGKEFLPMEAQLSRLIGQSLWDVSRSSTGNLVEWFLL  358
SEQ ID NO:4  WESGENLERVAKYSMEDAKATYELGKEFLPMEIQLSRLVGQPLWDVSRSSTGNLVEWFLL  358
SEQ ID NO:3  WETGKGLERVAKYSMEDAKVTYELGREFFPMEAQLSRLVGQPIWDVSRSSTGNLVEWYLL  358
SEQ ID NO:6  WETGKGLERVAKYSMEDAKVTFELGKEFFPMEAQLARLVGQPVWDVSRSSTGNLVEWFLL  358
             **: : :::** :******:.::***:**:***::*::*  :.:**********::*
```

FIG. 1 cont'd

```
SEQ ID NO:1  RKAYKRNELAPNKPDERELARR-RGGYAGGYVKEPERGLWDNIVYLDFRSLYPSIIITHN  417
SEQ ID NO:2  RVAYARNELAPNKPDEEEYKRRLRTTYLGGYVKEPEKGLWENITYLDFRSLYPSIIVTHN  420
SEQ ID NO:7  RKAYERNELAPNKPDERELARR-AESYAGGYVKEPEKGLWENIVYLDYKSLYPSIIITHN  417
SEQ ID NO:5  RKAYERNELAPNKPDEKELARR-RQSYEGGYVKEPERGLWENIVYLDFRSLYPSIIITHN  417
SEQ ID NO:4  RKAYERNEVAPNKPSEEEYQRRLRESYTGGFVKEPEKGLWENIVYLDFRALYPSIIITHN  418
SEQ ID NO:3  RKAYERNELAPNKPDEREYERRLRESYAGGYVKEPEKGLWEGIVSLDFRSLYPSIIITHN  418
SEQ ID NO:6  RKAYERNELAPNKPDEREYERRLRESYEGGYVKEPEKGLWEGIVSLDFRSLYPSIIITHN  418
              *.* :***:****  *:   *. ****:*:****. **. *****.

SEQ ID NO:1  VSPDTLNREGCKEYDVAPEVGHKFECKDFPGFIPSLLGDLLEERQKIKRRMKATVDPLEKK  477
SEQ ID NO:2  VSPDTLEKEGCKNYDVAPIVGYPKARWYSKECAESVTAWGRHYIEMTIRELEEKFGFKVL  480
SEQ ID NO:7  VSPDTLNREGCKNYDVAPIVGYRFCKDFPGFIPSILGDLIAMRQDIKKKMKSTIDPIEKK  477
SEQ ID NO:5  VSPDTLNREGCREYDVAPQVGHRFCKDFPGFIPSLLGDFLEERQKVKKRMKATVDPIERK  477
SEQ ID NO:4  VSPDTLNREGCKEYDVAPQVGHRFCKDFPGFIPSLLGDLLEERQKIKKKMKATIDPIERK  478
SEQ ID NO:3  VSPDTLNLEGCKNYDIAPQVGHRFCKDIPGFIPSLLGHLLEERQKIKTKMKETQDPIEKI  478
SEQ ID NO:6  VSPDTLNRENCKEYDVAPQVGHRFCKDFPGFIPSLLKRLLDERQEIKRKMKASKDPIEKK  478
              ******  .*: **.** **:: ***:*******  :  *:*.:  :*  *   ::*

SEQ ID NO:1  LLDYRQRAIKILANSFYGYYGYAKARWYCKECAESVTAWGREYIEMVIRELEEKFGFKVL  537
SEQ ID NO:2  MLDYRORAIKLLANSYYGMGYPKARWYSKECAESVTAWGRHYIEMTIRELEEKFGFKVL  540
SEQ ID NO:7  LLDYRORAIKILANSYYGIYGYANARWYCRECAESVTAWGRQYIETTMRETEEKFGFKVI  537
SEQ ID NO:5  LLDYRQRAIKLLANSYYGVYGYARARWYCKECAESVTAWGREYITMTIKELEEKYGFKVI  537
SEQ ID NO:4  LLDYRORAIKILANSFYGVYGYAKARWYCKECAESVTAWGRKYIELVWKELEEKGFKVL  538
SEQ ID NO:3  MLDYRQRAIKLLANSYYGVYGYARARWYCKECAESVTAWGREYIEFVRKELEEKFGFKVL  538
SEQ ID NO:6  LLDYRQRAIKILANSYYGVYGYAKARWYCKECAESVTAWGROYIDLVRRELES-RGFKVL  537
              :****:***: ***:**: ***:****.:**********: **   ::**    ****:
```

FIG. 1 cont'd

```
SEQ ID NO:1  YADTDGLHATIPGADAETVKKKAKEFLKYINPKLPGLLELEYEGFYVRGFFVTKKKYAVI  597
SEQ ID NO:2  YADTDGFYATIPGEKPELIKKKAKEFLNYINSKLPGLLELEYEGFYLRGFFVTKKRYAVI  600
SEQ ID NO:7  YADTDGFFATIPGADAETVKKKTKEFLNYINPRLPGLLELEYEGFYRRGFFVTKKKYAVI  597
SEQ ID NO:5  YSDTDGFFATIPGADAETVKKKAMEFLKYINAKLPGALELEYEGFYKRGFFVTKKKYAVI  597
SEQ ID NO:4  YIDTDGLYATIPGGESEEIKKKALEFVKYINSKLPGLLELEYEGFYKRGFFVTKKKYAVI  598
SEQ ID NO:3  YIDTDGLYATIPGAKPEEIKKKALEFVDYINAKLPGLLELEYEGFYVRGFFVTKKKYALI  598
SEQ ID NO:6  YIDTDGLYATIPGAKHEEIKEKALKFVEYINSKLPGLLELEYEGFYARGFFVTKKKYALI  597
             * ****:.***** :*:*:::** *.:.:***  ***************.*****:*::

SEQ ID NO:1  DEEGKITTRGLEIVRRDWSEIAKETQARVLEAILKHGDVEEAVRIVKEVTEKLSKYEVPP  657
SEQ ID NO:2  DEEGKRITTRGLEIVRRDWSEIAKETQAKVLEAILKHGEGSVEKAVEVVRDVVEKIAKYRVPL  660
SEQ ID NO:7  DEEDKITTRGLEIVRRDWSEIAKETQARVLEAILKHGDVEEAVRIVKEVTEKLSRYEVPP  657
SEQ ID NO:5  DEEEGKITTRGLEIVRRDWSEIAKETQARVLEAILKDGDVEKAVRIVKEVTEKLSKYEVPP  657
SEQ ID NO:4  DEEGKVITRGLEIVRRDWSEIAKETQARVLETILKHGDVEEAVRIVKEVIQKLANYEIPF  658
SEQ ID NO:3  DEEGKIITTRGLEIVRRDWSEIAKETQAKVLEAILKHGNVEEAVKIVKEVTEKLSKYEIPP  658
SEQ ID NO:6  DEEGKIVTRGLEIVRRDWSEIAKETQAKVLEAILKHGNVDEAVKIVKEVTEKLSKYEIPP  657
             ***.: .:: :*******  :.**** * :::*: :.**:::.*  :.**  :*

SEQ ID NO:1  EKLVIHEQITRDLRDYKATGPHVAVAKRLAARGVKIRPGTVISYIVLKGSGRIGDRAIPA  717
SEQ ID NO:2  EKLIHEQITRDLKDYKAIGPHVAIAKRLAARGIKVKPGTIISYIVLKGSGKISDRVILL  720
SEQ ID NO:7  EKLVIYEQITRNLRDYKATGPHVAVAKRLAARGIKIRPGTVISYIVLKGPGRVGDRAIPF  717
SEQ ID NO:5  EKLVIHEQITRDLKDYKATGPHVAVAKRLAARGVKIRPGTVISYIVLKGSGRIGDRAIPF  717
SEQ ID NO:4  EKLAIYEQITRPLHEYKAIGPHVAVAKRLAAKGVKIRPGMVIGYIVLRGDGPISNRAILA  718
SEQ ID NO:3  EKLVIYEQITRPLHEYKAIGPHVAVAKRLAAKGVKVRPGMVIGYIVLRGDGPISKRAILA  718
SEQ ID NO:6  EKLVIYEQITRPLSEYKAIGPHVAVAKRLAAKGVKVKPGMVIGYIVLRGDGPISKRAIAI  717
             ***.*:****.* :** .******.****:*:*::**:::.*:.**  .:: .**
```

FIG. 1 cont'd

```
SEQ ID NO: 1  DEFDPTKHRYDAEYYIENQVLPAVERILKAFGYRKEDLRYQKTKQVGLGAWLKVKGKK-  775
SEQ ID NO: 2  TEYDPRKHKYDPDYYIENQVLPAVLRILEAFGYRKEDLRYQSSKQTGLDAWLKR----  774
SEQ ID NO: 7  DEFDPAKHRYDAEYYIENQVLPAVLRILEAFGYRKEDLRYQKTKQAGLGAWLKPKTGS-  775
SEQ ID NO: 5  DEFDPTKHKYDAEYYIENQVLPAVERILRAFGYRKEDLRYQKTRQVGLSAWLKPKGT--  774
SEQ ID NO: 4  EEYDPKKHKYDAEYYIENQVLPAVLRILEGFGYRKEDLRYQKTRQVGLTSWLNIKKS--  775
SEQ ID NO: 3  EEFDLRKHKYDAEYYIENQVLPAVLRILEAFGYRKEDLRWQKTKQTGLTAWLNIKKKGS  777
SEQ ID NO: 6  EEFDPKKHKYDAEYYIENQVLPAVERILRAFGYRKEDLKYQKTKQVGLGAWLKFGS---  773
              *.:  **.;** .:********.:******* :****:***;;:.:*.** :**:;
```

POLYMERASES, COMPOSITIONS, AND METHODS OF USE

PRIORITY

This application claims the benefit of U.S. Provisional Application No. 62/775,662, filed Dec. 5, 2018, the disclosure of which is incorporated by reference herein in its entirety.

SEQUENCE LISTING

This application contains a Sequence Listing electronically submitted via EFS-Web to the United States Patent and Trademark Office as an ASCII text file entitled "1727US01_ST25.txt" having a size of 112 kilobytes and created on Nov. 26, 2019. The information contained in the Sequence Listing is incorporated by reference herein.

FIELD

The present disclosure relates to, among other things, altered polymerases for use in performing a nucleotide incorporation reaction, particularly in the context of nucleic acid sequencing by synthesis.

BACKGROUND

Next-generation sequencing (NGS) technology relies on DNA polymerases as a critical component of the sequencing process. Reduction of the time for sequencing a template while maintaining high fidelity is desirable. Reducing each cycle of a sequencing by synthesis (SBS) process is a useful step to achieving a shorter sequencing run time. One approach to reduce cycle time is to reduce the time of the incorporation step. However, while reductions in incorporation time could offer significant improvement to the overall run time, they typically do so at the expense of fidelity. For instance, phasing rates, pre-phasing rates, and/or bypass rates increase, and as a consequence error rate is increased. At low error rates, during a sequencing run most template molecules in a cluster terminate in the same labeled nucleotide and the signal is clear. In contrast, at reduced fidelity, during a sequencing run an increasing number of template molecule in a cluster terminate in the incorrect labeled nucleotide and the signal can become too noisy to accurately determine which nucleotide was incorporated.

SUMMARY

Provided herein are recombinant DNA polymerases. One example of a polymerase of the present disclosure includes an amino acid sequence that is at least 80% identical to a 9°N DNA polymerase amino acid sequence SEQ ID NO:1.

Another example of a polymerase of the present disclosure of a DNA polymerase includes an amino acid sequence that is at least 80% identical to a 9°N DNA polymerase amino acid sequence SEQ ID NO:1, and an amino acid substitution mutation at a position functionally equivalent to Ala281, Phe283, Thr349, or Trp397 in the 9°N DNA polymerase amino acid sequence.

In one embodiment, a DNA polymerase includes an amino acid sequence that is at least 80% identical to a 9°N DNA polymerase amino acid sequence SEQ ID NO:8, and an amino acid substitution mutation at a position functionally equivalent to Ala281Gly, Ala281Phe, Phe283 Ser, Thr349Ser, Thr349Asn, Thr349Lys, Trp397Cys, Trp397Phe, or His633Thr in the 9°N DNA polymerase amino acid sequence. In one embodiment, a DNA polymerase includes the amino acid sequence of any one of SEQ ID NOs:9-17.

Also provided is a nucleic acid molecule encoding a polymerase described herein, an expression vector that includes the nucleic acid molecule, and a host cell that includes the vector.

Further provided are methods. In one embodiment, a method is for incorporating modified nucleotides into DNA, and includes allowing the following components to interact: (i) a polymerase described herein, (ii) a DNA template; and (iii) a nucleotide solution.

Also provided are kits. In one embodiment, a kit is for performing a nucleotide incorporation reaction. The kit can include a polymerase described herein and a nucleotide solution.

BRIEF DESCRIPTION OF THE DRAWINGS

FIG. 1 is a schematic showing alignment of polymerase amino acid sequences from *Thermococcus* sp. 9°N-7 (9°N, SEQ ID NO:1), *Thermococcus litoralis* (Vent, SEQ ID NO:2 and Deep Vent, SEQ ID NO:3), *Thermococcus waiotapuensis* (Twa, SEQ ID NO:7), *Thermococcus kodakaraensis* (KOD, SEQ ID NO:5), *Pyrococcus furiosus* (Pfu, SEQ ID NO:4), *Pyrococcus abyssi* (Pab, SEQ ID NO:6). An "*" (asterisk) indicates positions which have a single, fully conserved residue between all polymerases. A ":" (colon) indicates conservation between groups of strongly similar properties as below—roughly equivalent to scoring >0.5 in the Gonnet PAM 250 matrix. A "." (period) indicates conservation between groups of weakly similar properties as below—roughly equivalent to scoring=<0.5 and >0 in the Gonnet PAM 250 matrix.

DETAILED DESCRIPTION OF EXEMPLARY EMBODIMENTS

Figure 2:
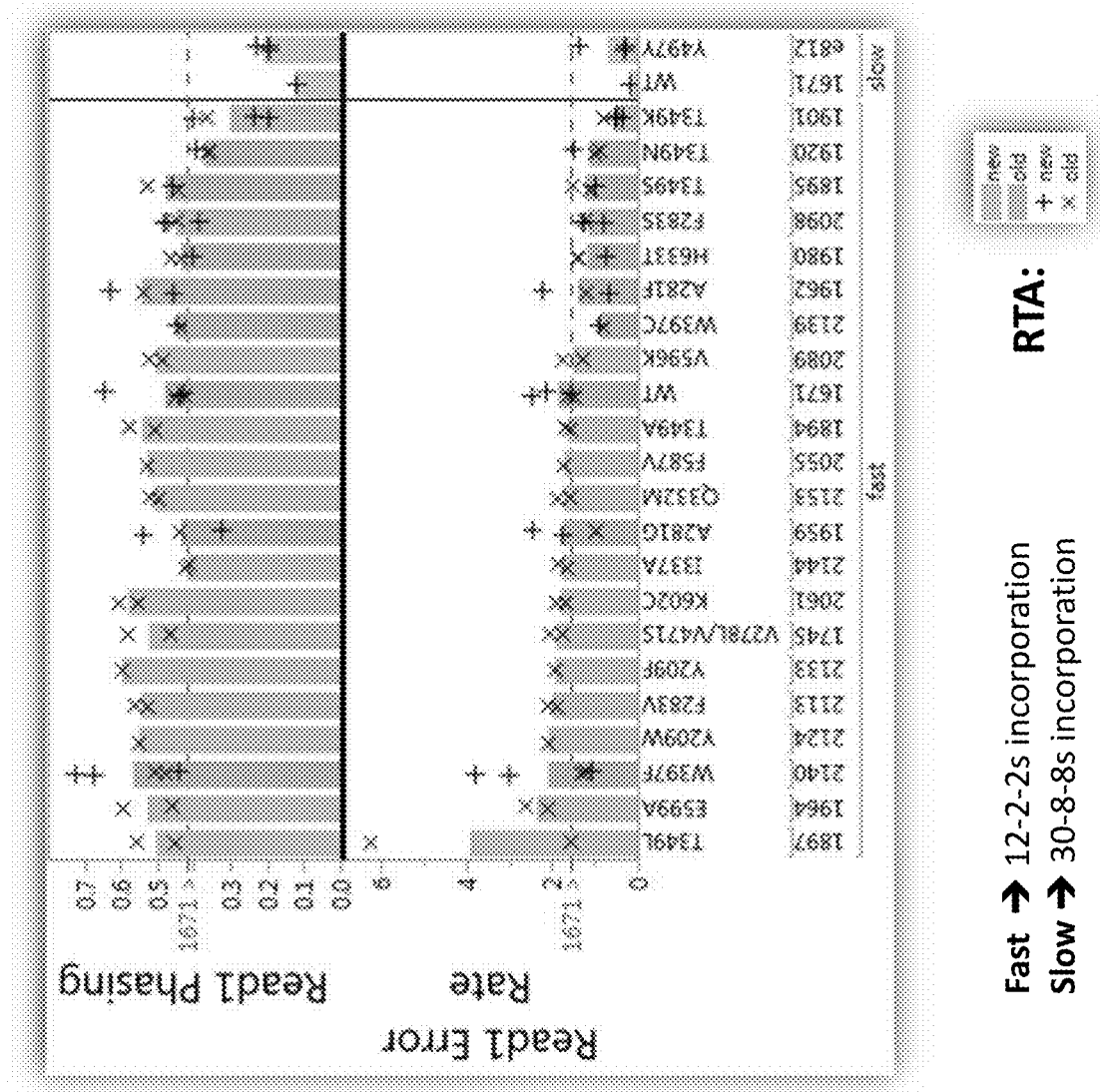
FIG. 2 shows the error rates and phasing levels of selected altered polymerases of the present disclosure. Starting at the bottom of the figure, "slow" refers to slow incorporation time, i.e., the standard incorporation time of 46 seconds; "fast" refers to the faster incorporation time of 16 seconds; "1671", "1901", etc., identify specific altered polymerases; WT, T349K, T349N, T349S, etc., refer to specific mutations in an altered polymerase relative to Pol 1671 ("WT" corresponds to Pol 1671 for the purposes of this application); and Pols 1671 and e812 refer to control polymerases.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Conditions that are "suitable" for an event to occur or "suitable" conditions are conditions that do not prevent such events from occurring. Thus, these conditions permit, enhance, facilitate, and/or are conducive to the event.

As used herein, "providing" in the context of a composition, an article, a nucleic acid, or a nucleus means making the composition, article, nucleic acid, or nucleus, purchasing the composition, article, nucleic acid, or nucleus, or otherwise obtaining the compound, composition, article, or nucleus.

Also herein, the recitations of numerical ranges by endpoints include all numbers subsumed within that range (e.g., 1 to 5 includes 1, 1.5, 2, 2.75, 3, 3.80, 4, 5, etc.).

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Maintaining or surpassing current levels of performance at faster incorporation times can be aided by a new generation of polymerases. Presented herein are polymerase enzymes having significantly improved performance under sequencing by synthesis (SBS) fast cycle time conditions. The inventors have surprisingly identified certain altered polymerases which exhibit improved characteristics including improved accuracy during short incorporations times. Improved accuracy includes reduced error rate and reduced phasing. The altered polymerases have a number of other associated advantages, including reduced prephasing, reduced bypass rate, and improved quality metrics in SBS reactions. This improvement is maintained even when a polymerase is used at lower concentrations. Accordingly, in one embodiment, the concentration of a DNA polymerase in an SBS reaction can be from 120 ng/µl to 80 ng/µl. In one embodiment, the concentration of a DNA polymerase in a SBS reaction can be no greater than 120 ng/µl, no greater than 110 ng/µl, no greater than 100 ng/µl, or no greater than 90 ng/µl. In one embodiment, the concentration of a DNA polymerase in an SBS reaction can be at least 80 ng/µl, at least 90 ng/µl, at least 100 ng/µl, or at least 110 ng/µl.

Error rate refers to a measurement of the frequency of error in the identification of the correct base, i.e., the complement of the template sequence at a specific position, during a sequencing reaction. The fidelity with which a sequenced library matches the original genome sequence can vary depending on the frequency of base mutation occurring at any stage from the extraction of the nucleic acid to its sequencing on a sequencing platform. This frequency places an upper limit on the probability of a sequenced base being correct. In some embodiments, the quality score is presented as a numerical value. For example, the quality score can be quoted as QXX where the XX is the score and it means that that particular call has a probability of error of $10^{-XX/10}$. Thus, as an example, Q30 equates to an error rate of 1 in 1000, or 0.1%, and Q40 equates to an error rate of 1 in 10,000, or 0.01%.

Phasing and pre-phasing are terms known to those of skill in the art and are used to describe the loss of synchrony in the readout of the sequence copies of a cluster. Phasing and pre-phasing cause the extracted intensities for a specific cycle to include the signal of the current cycle and noise from the preceding and following cycles. Thus, as used herein, the term "phasing" refers to a phenomenon in SBS that is caused by incomplete incorporation of a nucleotide in some portion of DNA strands within clusters by polymerases at a given sequencing cycle, and is thus a measure of the rate at which single molecules within a cluster lose sync with each other. Phasing can be measured during detection of cluster signal at each cycle and can be reported as a percentage of detectable signal from a cluster that is out of synchrony with the signal in the cluster. As an example, a cluster is detected by a "green" fluorophore signal during cycle N. In the subsequent cycle (cycle N+1), 99.9% of the cluster signal is detected in the "red" channel and 0.1% of the signal remains from the previous cycle and is detected in the "green" channel. This result would indicate that phasing is occurring, and can be reported as a numerical value, such as a phasing value of 0.1, indicating that 0.1% of the molecules in the cluster are falling behind at each cycle.

The term "pre-phasing" as used herein refers to a phenomenon in SBS that is caused by the incorporation of nucleotides without effective 3' terminators, causing the incorporation event to go one cycle ahead. As the number of cycles increases, the fraction of sequences per cluster affected by phasing increases, hampering the identification of the correct base. Pre-phasing can be detected by a sequencing instrument and reported as a numerical value, such as a pre-phasing value of 0.1, indicating that 0.1% of the molecules in the cluster are running ahead at each cycle.

Detection of phasing and pre-phasing can be performed and reported according to any suitable methodology as is known in the art, for example, as described in U.S. Pat. No. 8,965,076 and U.S. Provisional Patent No. 62/535,558. For example, as described in the Examples below, phasing is detected and reported routinely during SBS sequencing runs on sequencing instrument such as HiSeq™, Genome Analyzer™, NextSeq™, NovaSeq™, iSeq™, MiniSeq™, or MiSeq™ sequencing platforms from Illumina, Inc. (San Diego, Calif.) or any other suitable instrument known in the art.

Reduced cycle times can increase the occurrence of phasing, pre-phasing, and/or bypass rate, each of which contributes to error rate. The discovery of altered polymerases which decrease the incidence of phasing, pre-phasing, and/or bypass rate, even when used in fast cycle time conditions, is surprising and provides a great advantage in SBS applications. For example, the altered polymerases can provide faster SBS cycle time, lower phasing and pre-phasing values, and/or longer sequencing read length. The characterization of error rate and phasing for altered polymerases as provided herein is set forth in the Example section below.

Polymerases

Provided herein are polymerases, compositions including a polymerase, and methods of using a polymerase. A polymerase described herein is a DNA polymerase. In one embodiment, a polymerase of the present disclosure, also referred to herein as an "altered polymerase," is based on the amino acid sequence of a reference polymerase. An altered polymerase includes substitution mutations at one or more residues when compared to the reference polymerase. A substitution mutation can be at the same position or a functionally equivalent position compared to the reference polymerase. Reference polymerases and functionally equivalent positions are described in detail herein. The skilled person will readily appreciate that an altered polymerase described herein is not naturally occurring.

A reference polymerase described herein has error rates that are useful is SBS reactions; however, using a reference polymerase in SBS reactions with shorter incorporation times increases the error rate. An altered polymerase described herein maintains the superior error rates observed with reference polymerases even when the altered polymerase is used in SBS reactions with shorter incorporation times. In one embodiment, reduced error rates occur when the altered polymerase is tested using fast incorporation times. Incorporation refers to the amount of time a DNA polymerase is in contact with a template. As used herein, a slow incorporation time is the incorporation time used under a standard cycle using a Min Seq™ benchtop sequencing system. Slow incorporation times include from 40 seconds to 50 seconds. As used herein, a fast cycle time refers to an incorporation step that is from 10 seconds to 40 seconds. In one embodiment, a fast cycle time is an incorporation time of no greater than 40 seconds, no greater than 30 seconds, no greater than 20 seconds, no greater than 18 seconds, no greater than 16 seconds, no greater than 14 seconds, or no greater than 12 seconds. In one embodiment, a fast cycle time is an incorporation time of at least 10 seconds, at least 12 seconds, at least 14 seconds, at least 16 seconds, at least 18 seconds, at least 20 seconds, or at least 30 seconds. In one embodiment, a fast cycle time is an incorporation time of less than 40 seconds, less than 30 seconds, less than 20 seconds, less than 18 seconds, less than 16 seconds, less than 14 seconds, less than 12 seconds, or less than 10 seconds.

An altered polymerase described herein can be used in SBS reactions for runs of different lengths. A "run" refers to the number of nucleotides that are identified on a template. A run typically includes a run based on the first primer (e.g., a read1 primer) which reads one strand of a template and a run based on the second primer (e.g., a read2 primer) which reads the complementary strand of the template. In one embodiment, the number of nucleotides identified using the first primer or the second primer can be from 10 to 150 nucleotides. In one embodiment, the number of nucleotides identified using the first primer or the second primer can be no greater than 150 nucleotides, no greater than 130 nucleotides, no greater than 110 nucleotides, no greater than 90 nucleotides, no greater than 70 nucleotides, no greater than 50 nucleotides, no greater than 30 nucleotides, or no greater than 20 nucleotides. In one embodiment, the number of nucleotides identified using the first primer or the second primer can be at least 10, at least 20, at least 30, at least 50, at least 70, at least 90, at least 110, or at least 130 nucleotides.

In certain embodiments, an altered polymerase is based on a family B type DNA polymerase. An altered polymerase can be based on, for example, a family B archaeal DNA polymerase, a human DNA polymerase-a, or a phage polymerase.

Family B archaeal DNA polymerases are well known in the art as exemplified by the disclosure of U.S. Pat. No. 8,283,149. In certain embodiments, an archaeal DNA polymerase is from a hyperthermophilic archaeon and is thermostable.

In certain embodiments, a family B archaeal DNA polymerase is from a genus such as, for example, *Thermococcus*, *Pyrococcus*, or *Methanococcus*. Members of the genus *Thermococcus* are well known in the art and include, but are not limited to T 4557, *T. barophilus*, *T. gammatolerans*, *T. onnurineus*, *T. sibiricus*, *T. kodakarensis*, *T. gorgonarius*, and *T. waiotapuensis*. Members of the genus *Pyrococcus* are well known in the art and include, but are not limited to P. NA2, *P. abyssi*, *P. furiosus*, *P. horikoshii*, *P. yayanosii*, *P. endeavori*, *P. glycovorans*, and *P. woesei*. Members of the genus *Methanococcus* are well known in the art and include, but are not limited to *M. aeolicus*, *M. maripaludis*, *M. vannielii*, *M. voltae*, *M. thermolithotrophicus*, and *M. jannaschii*.

In one embodiment an altered polymerase is based on Vent®, Deep Vent®, 9°N, Pfu, KOD, or a Pab polymerase. Vent® and Deep Vent® are commercial names used for family B DNA polymerases isolated from the hyperthermophilic archaeon *Thermococcus litoralis*. 9°N polymerase is a family B polymerase isolated from *Thermococcus* sp. Pfu polymerase is a family B polymerase isolated from *Pyrococcus furiosus*. KOD polymerase is a family B polymerase isolated from *Thermococcus kodakaraenis*. Pab polymerase is a family B polymerase isolated from *Pyrococcus abyssi*. Twa is a family B polymerase isolated from *T. waiotapuensis*. Examples of Vent®, Deep Vent®, 9°N, Pfu, KOD, Pab, and Twa polymerases are disclosed in FIG. 1.

In certain embodiments, a family B archaeal DNA polymerase is from a phage such as, for example, T4, RB69, or phi29 phage.

FIG. 1 shows a sequence alignment for proteins having the amino acid sequences shown in SEQ ID NOs:1-7. The alignment indicates amino acids that are conserved in the different family B polymerases. The skilled person will appreciate that the conserved amino acids and conserved regions are most likely conserved because they are important to the function of the polymerases, and therefore show a correlation between structure and function of the polymerases. The alignment also shows regions of variability across the different family B polymerases. A person of ordinary skill in the art can deduce from such data regions of a polymerase in which substitutions, particularly conservative substitutions, may be permitted without unduly affecting biological activity of the altered polymerase.

An altered polymerase described herein is based on the amino acid sequence of a known polymerase (also referred to herein as a reference polymerase) and further includes substitution mutations at one or more residues. In one embodiment, a substitution mutation is at a position functionally equivalent to an amino acid of a reference polymerase. By "functionally equivalent" it is meant that the altered polymerase has the amino acid substitution at the amino acid position in the reference polymerase that has the same functional role in both the reference polymerase and the altered polymerase.

In general, functionally equivalent substitution mutations in two or more different polymerases occur at homologous amino acid positions in the amino acid sequences of the polymerases. Hence, use herein of the term "functionally equivalent" also encompasses mutations that are "positionally equivalent" or "homologous" to a given mutation, regardless of whether or not the particular function of the mutated amino acid is known. It is possible to identify the locations of functionally equivalent and positionally equivalent amino acid residues in the amino acid sequences of two or more different polymerases on the basis of sequence alignment and/or molecular modelling. An example of sequence alignment to identify positionally equivalent and/or functionally equivalent residues is set forth in FIG. 1. For example, the residues in the Twa, KOD, Pab, Pfu, Deep Vent, and Vent polymerases of FIG. 1 that are vertically aligned are considered positionally equivalent as well as functionally equivalent to the corresponding residue in the 9°N polymerase amino acid sequence. Thus, for example residue 349 of the 9°N, Twa, KOD, Pfu, Deep Vent, and Pab polymerases and residue 351 of the Vent polymerase are functionally equivalent and positionally equivalent. Likewise, for example residue 633 of the 9°N, Twa, KOD, and Pab polymerases, residue 634 of the Pfu and Deep Vent polymerases, and residue 636 of the Vent polymerase are functionally equivalent and positionally equivalent. The skilled person can easily identify functionally equivalent residues in DNA polymerases.

In certain embodiments, the substitution mutation comprises a mutation to a residue having a non-polar side chain. Amino acids having non-polar side chains are well-known in the art and include, for example: alanine, glycine, isoleucine, leucine, methionine, phenylalanine, proline, tryptophan, and valine.

In certain embodiments, the substitution mutation comprises a mutation to a residue having a polar side chain. Amino acids having polar side chains are well-known in the art and include, for example: arginine, asparagine, aspartic acid, glutamine, glutamic acid, histidine, lysine, serine, cysteine, tyrosine, and threonine.

In certain embodiments, the substitution mutation comprises a mutation to a residue having a hydrophobic side chain. Amino acids having hydrophobic side chains are well-known in the art and include, for example: glycine, alanine, valine, leucine, isoleucine, proline, phenylalanine, methionine, and tryptophan.

In certain embodiments, the substitution mutation comprises a mutation to a residue having an uncharged side chain. Amino acids having uncharged side chains are well-known in the art and include, for example: glycine, serine, cysteine, asparagine, glutamine, tyrosine, and threonine, among others.

In one embodiment, an altered polymerase has an amino acid sequence that is structurally similar to a reference polymerase disclosed herein. In one embodiment, a reference polymerase is one that includes the amino acid sequence of 9°N (SEQ ID NO:1). In one embodiment, the reference polymerase is SEQ ID NO:1 with the following substitution mutations: Met129Ala, Asp141Ala, Glu143Ala, Cys223Ser, Leu408Ala, Tyr409Ala, Pro410Ile, Ala485Val, Tyr497Gly, Arg247Tyr, Glu599Asp, and His633Gly. This second reference polymerase is disclosed at SEQ ID NO:8, and is also referred to herein as the Pol 1671 polymerase. Other reference sequences include SEQ ID NO:2, 3, 4, 5, 6, or 7. Optionally, a reference polymerase is SEQ ID NO: 2, 3, 4, 5, 6, or 7 with substitution mutations functionally equivalent to the following substitution mutations in SEQ ID NO:1: Met129Ala, Asp141Ala, Glu143Ala, Cys223Ser, Leu408Ala, Tyr409Ala, Pro410Ile, Ala485Val, Tyr497Gly, Arg247Tyr, Glu599Asp, and His633Gly.

As used herein, an altered polymerase may be "structurally similar" to a reference polymerase if the amino acid sequence of the altered polymerase possesses a specified amount of sequence similarity and/or sequence identity compared to the reference polymerase.

Structural similarity of two amino acid sequences can be determined by aligning the residues of the two sequences (for example, a candidate polymerase and a reference polymerase described herein) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate polymerase is the polymerase being compared to the reference polymerase. A candidate polymerase that has structural similarity with a reference polymerase and polymerase activity is an altered polymerase.

Unless modified as otherwise described herein, a pairwise comparison analysis of amino acid sequences or nucleotide sequences can be conducted, for instance, by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Current Protocols in Molecular Biology, Ausubel et al., eds., Current Protocols, a joint venture between Greene Publishing Associates, Inc. and John Wiley & Sons, Inc., supplemented through 2004).

One example of an algorithm that is suitable for determining structural similarity is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., J. Mol. Biol. 215:403-410 (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a protein may be selected from other members of the class to which the amino acid belongs. For example, it is well-known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with biological activity. For example, non-polar amino acids include alanine, glycine, isoleucine, leucine, methionine, phenylalanine, proline, tryptophan, and valine. Hydrophobic amino acids include glycine, alanine, valine, leucine, isoleucine, proline, phenylalanine, methionine, and tryptophan. Polar amino acids include arginine, asparagine, aspartic acid, glutamine, glutamic acid, histidine, lysine, serine, cysteine, tyrosine, and threonine. The uncharged amino acids include glycine, serine, cysteine, asparagine, glutamine, tyrosine, and threonine, among others.

Thus, as used herein, reference to a polymerase as described herein, such as reference to the amino acid sequence of one or more SEQ ID NOs described herein can include a protein with at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the reference polymerase.

Alternatively, as used herein, reference to a polymerase as described herein, such as reference to the amino acid sequence of one or more SEQ ID NOs described herein can include a protein with at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference polymerase.

The present disclosure describes a collection of mutations that result in a polymerase having one or more of the activities described herein. A polymerase described herein can include any number of mutations, e.g., at least 1, at least 2, at least 3, at least 4, at least 5, at least 6, at least 7, at least 8, at least 9, at least 10, at least 11, at least 12, at least 13, at least 14, at least 15, at least 16, at least 17, or at least 18 mutations compared to a reference polymerase, such as SEQ ID NO:1 or SEQ ID NO:8. Likewise, a polymerase described herein can include the mutations in any combination.

In one embodiment, an altered polymerase includes a substitution mutation at a position functionally equivalent to Ala281 in a 9°N polymerase (SEQ ID NO:1). In one embodiment, the substitution mutation at a position functionally equivalent to Ala281 is a mutation to a non-polar, hydrophobic, or uncharged amino acid, for example Gly or Phe.

In one embodiment, an altered polymerase includes a substitution mutation at a position functionally equivalent to Phe283 in a 9°N polymerase (SEQ ID NO:1). In one embodiment, the substitution mutation at a position functionally equivalent to Phe283 is a mutation to a polar or uncharged amino acid, for example Ser.

In one embodiment, an altered polymerase includes a substitution mutation at a position functionally equivalent to Thr349 in a 9°N polymerase (SEQ ID NO:1). In one embodiment, the substitution mutation at a position functionally equivalent to Thr349 is a mutation to a polar or uncharged amino acid, for example Ser, Asn, or Lys.

In one embodiment, an altered polymerase includes a substitution mutation at a position functionally equivalent to Trp397 in a 9°N polymerase (SEQ ID NO:1). In one embodiment, the substitution mutation at a position functionally equivalent to Trp397 is a mutation to a polar or uncharged amino acid, for example Cys.

In one embodiment, an altered polymerase includes a substitution mutation at a position functionally equivalent to Trp397 in a 9°N polymerase (SEQ ID NO:1). In one embodiment, the substitution mutation at a position functionally equivalent to Trp397 is a mutation to a non-polar or hydrophobic amino acid, for example Phe.

In one embodiment, an altered polymerase includes a substitution mutation at a position functionally equivalent to His633 in a 9°N polymerase (SEQ ID NO:1). In one embodiment, the substitution mutation at a position functionally equivalent to His633 is a mutation to a polar or uncharged amino acid, for example Thr.

In one embodiment, an altered polymerase includes at least two, at least three, at least four, or five substitutions mutations at a position functionally equivalent to Ala281, Phe283, Thr349, Trp397, or His633 in a 9°N polymerase (SEQ ID NO:1).

In one embodiment, an altered polymerase includes a substitution mutation at a position functionally equivalent to Arg247 in a 9°N polymerase (SEQ ID NO:1). In one embodiment, the substitution mutation at a position functionally equivalent to Arg247 is a mutation to a polar or uncharged amino acid, for example Tyr.

In one embodiment, an altered polymerase includes a substitution mutation at a position functionally equivalent to Tyr497 in a 9°N polymerase (SEQ ID NO:1). In one embodiment, the substitution mutation at a position functionally equivalent to Tyr497 is a mutation to a non-polar, hydrophobic, or uncharged amino acid, for example Gly.

In one embodiment, an altered polymerase includes a substitution mutation at a position functionally equivalent to Glu599 in a 9°N polymerase (SEQ ID NO:1). In one embodiment, the substitution mutation at a position functionally equivalent to Glu599 is a mutation to a polar amino acid, for example Asp.

In one embodiment, an altered polymerase includes a substitution mutation at a position functionally equivalent to Lys620 in a 9°N polymerase (SEQ ID NO:1). In one embodiment, the substitution mutation at a position functionally equivalent to Lys620 is a mutation to a polar or uncharged amino acid, for example Arg.

In one embodiment, an altered polymerase includes a substitution mutation at a position functionally equivalent to His633 in a 9°N polymerase (SEQ ID NO:1), wherein the mutation is to Gly.

In one embodiment, an altered polymerase includes a substitution mutation at a position functionally equivalent to Val661 in a 9°N polymerase (SEQ ID NO:1). In one embodiment, the substitution mutation at a position functionally equivalent to Val661 is a mutation to a polar or uncharged amino acid, for example Asp.

In one embodiment, an altered polymerase includes at least one, at least two, at least three, at least four, or five substitution mutation at a position functionally equivalent to an amino acid at Ala281, Phe283, Thr349, Trp397, or His633, a substitution mutation at a position functionally equivalent to Tyr497, and at least one, at least two, at least three, at least four, or five substitution mutations at a position functionally equivalent to an amino acid at Arg247, Glu599, Lys620, or Val661 in a 9°N polymerase (SEQ ID NO:1).

In one embodiment, an altered polymerase includes a substitution mutation at a position functionally equivalent to Met129 in a 9°N polymerase (SEQ ID NO:1). In one embodiment, the substitution mutation at a position functionally equivalent to Met129 is a mutation to a non-polar or hydrophobic amino acid, for example Ala.

In one embodiment, an altered polymerase includes a substitution mutation at a position functionally equivalent to Asp141 in a 9°N polymerase (SEQ ID NO:1). In one embodiment, the substitution mutation at a position functionally equivalent to Asp141 is a mutation to a non-polar or hydrophobic amino acid, for example Ala.

In one embodiment, an altered polymerase includes a substitution mutation at a position functionally equivalent to Glu143 in a 9°N polymerase (SEQ ID NO:1). In one embodiment, the substitution mutation at a position functionally equivalent to Glu143 is a mutation to a non-polar or hydrophobic amino acid, for example Ala.

In one embodiment, an altered polymerase includes a substitution mutation at a position functionally equivalent to Cys223 in a 9°N polymerase (SEQ ID NO:1). In one embodiment, the substitution mutation at a position functionally equivalent to Cys223 is a mutation to a polar or uncharged amino acid, for example Ser.

In one embodiment, an altered polymerase includes a substitution mutation at a position functionally equivalent to Lys408 in a 9°N polymerase (SEQ ID NO:1). In one embodiment, the substitution mutation at a position functionally equivalent to Lys408 is a mutation to a non-polar or hydrophobic amino acid, for example Ala.

In one embodiment, an altered polymerase includes a substitution mutation at a position functionally equivalent to Tyr409 in a 9°N polymerase (SEQ ID NO:1). In one embodiment, the substitution mutation at a position functionally equivalent to Tyr409 is a mutation to a non-polar or hydrophobic amino acid, for example Ala.

In one embodiment, an altered polymerase includes a substitution mutation at a position functionally equivalent to Pro410 in a 9°N polymerase (SEQ ID NO:1). In one embodiment, the substitution mutation at a position functionally equivalent to Pro410 is a mutation to a non-polar or hydrophobic amino acid, for example Ile.

In one embodiment, an altered polymerase includes a substitution mutation at a position functionally equivalent to Ala485 in a 9°N polymerase (SEQ ID NO:1). In one embodiment, the substitution mutation at a position functionally equivalent to Ala485 is a mutation to a non-polar or hydrophobic amino acid, for example Val.

In one embodiment, an altered polymerase includes at least one, at least two, at least three, at least four, or five substitution mutation at a position functionally equivalent to an amino acid at Ala281, Phe283, Thr349, Trp397, or His633, a substitution mutation at a position functionally equivalent to Tyr497, at least one, at least two, at least three, at least four, or five substitution mutations at a position functionally equivalent to an amino acid at Arg247, Glu599, His633, Lys620, or Val661, and at least one, at least two, at least three, at least four, at least five, at least six, at least seven, or eight substitution mutation at a position functionally equivalent to amino acid Met129, Asp141, Glu143, Cys223, Lys408, Tyr409, Pro410, or Ala485 in a 9°N polymerase (SEQ ID NO:1).

In one embodiment, an altered polymerase includes an amino acid sequence that is at least 80% identical to a 9°N DNA polymerase amino acid sequence SEQ ID NO:8, wherein the polymerase includes an amino acid substitution mutation at a position functionally equivalent to Ala281Gly in the 9°N DNA polymerase amino acid sequence.

In one embodiment, an altered polymerase includes an amino acid sequence that is at least 80% identical to a 9°N DNA polymerase amino acid sequence SEQ ID NO:8, wherein the polymerase includes an amino acid substitution mutation at a position functionally equivalent to Ala281Phe in the 9°N DNA polymerase amino acid sequence.

In one embodiment, an altered polymerase includes an amino acid sequence that is at least 80% identical to a 9°N DNA polymerase amino acid sequence SEQ ID NO:8, wherein the polymerase includes an amino acid substitution mutation at a position functionally equivalent to Phe283 Ser in the 9°N DNA polymerase amino acid sequence.

In one embodiment, an altered polymerase includes an amino acid sequence that is at least 80% identical to a 9°N DNA polymerase amino acid sequence SEQ ID NO:8, wherein the polymerase includes an amino acid substitution mutation at a position functionally equivalent to Thr349Ser in the 9°N DNA polymerase amino acid sequence.

In one embodiment, an altered polymerase includes an amino acid sequence that is at least 80% identical to a 9°N DNA polymerase amino acid sequence SEQ ID NO:8, wherein the polymerase includes an amino acid substitution mutation at a position functionally equivalent to Thr349Asn in the 9°N DNA polymerase amino acid sequence.

In one embodiment, an altered polymerase includes an amino acid sequence that is at least 80% identical to a 9°N DNA polymerase amino acid sequence SEQ ID NO:8, wherein the polymerase includes an amino acid substitution mutation at a position functionally equivalent to Thr349Lys in the 9°N DNA polymerase amino acid sequence.

In one embodiment, an altered polymerase includes an amino acid sequence that is at least 80% identical to a 9°N DNA polymerase amino acid sequence SEQ ID NO:8, wherein the polymerase includes an amino acid substitution mutation at a position functionally equivalent to Trp397Cys in the 9°N DNA polymerase amino acid sequence.

In one embodiment, an altered polymerase includes an amino acid sequence that is at least 80% identical to a 9°N DNA polymerase amino acid sequence SEQ ID NO:8, wherein the polymerase includes an amino acid substitution mutation at a position functionally equivalent to Trp397Phe in the 9°N DNA polymerase amino acid sequence.

In one embodiment, an altered polymerase includes an amino acid sequence that is at least 80% identical to a 9°N DNA polymerase amino acid sequence SEQ ID NO:8, wherein the polymerase includes an amino acid substitution mutation at a position functionally equivalent to His633Thr in the 9°N DNA polymerase amino acid sequence.

Specific examples of altered polymerases include Pol 1895 (SEQ ID NO:9), Pol 1901 (SEQ ID NO:10), Pol 1920 (SEQ ID NO:11), Pol 1959 (SEQ ID NO:12), Pol 1962 (SEQ ID NO:13), Pol 1980 (SEQ ID NO:14), Pol 2098 (SEQ ID NO:15), Pol 2139 (SEQ ID NO:16), and Pol 2140 (SEQ ID NO:17).

An altered polymerase described herein can include additional mutations that are known to affect polymerase activity. On such substitution mutation is at a position functionally equivalent to Arg713 in the 9°N polymerase (SEQ ID NO:1). Any of a variety of substitution mutations at one or more of positions known to result in reduced exonuclease activity can be made, as is known in the art and exemplified by U.S. Pat. No. 8,623,628. In one embodiment, the substitution mutation at position Arg713 is a mutation to a non-polar, hydrophobic, or uncharged amino acid, for example Gly, Met, or Ala.

In one embodiment, an altered polymerase includes a substitution mutation at a position functionally equivalent to Arg743 or Lys705, or a combination thereof, in the 9°N polymerase (SEQ ID NO:1), as is known in the art and exemplified by the disclosure of U.S. Pat. No. 8,623,628. In one embodiment, the substitution mutation at position Arg743 or Lys705 is a mutation to a non-polar or hydrophobic amino acid, for example Ala.

The present disclosure also provides compositions that include an altered polymerase described herein. The composition can include other components in addition to the altered polymerase. For example, the composition can include a buffer, a nucleotide solution, or a combination thereof. The nucleotide solution can include nucleotides, such as nucleotides that are labelled, synthetic, modified, or a combination thereof. In one embodiment, a composition includes target nucleic acids, such as a library of target nucleic acids.

Mutating Polymerases

Various types of mutagenesis are optionally used in the present disclosure, e.g., to modify polymerases to produce variants, e.g., in accordance with polymerase models and model predictions as discussed above, or using random or semi-random mutational approaches. In general, any available mutagenesis procedure can be used for making polymerase mutants. Such mutagenesis procedures optionally include selection of mutant nucleic acids and polypeptides for one or more activity of interest (e.g., reduced pyrophosphorolysis, increased turnover e.g., for a given nucleotide analog). Procedures that can be used include, but are not limited to: site-directed point mutagenesis, random point mutagenesis, in vitro or in vivo homologous recombination (DNA shuffling and combinatorial overlap PCR), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, degenerate PCR, double-strand break repair, and many others known to persons of skill. The starting polymerase for mutation can be any of those noted herein, including available polymerase mutants such as those identified e.g., in U.S. Pat. Nos. 8,460,910 and 8,623,628, each of which is incorporated by reference in its entirety.

Optionally, mutagenesis can be guided by known information from a naturally occurring polymerase molecule, or of a known altered or mutated polymerase (e.g., using an existing mutant polymerase), e.g., sequence, sequence comparisons, physical properties, crystal structure and/or the like as discussed above. However, in another class of embodiments, modification can be essentially random (e.g., as in classical or "family" DNA shuffling, see, e.g., Crameri et al. (1998) "DNA shuffling of a family of genes from diverse species accelerates directed evolution" Nature 391:288-291).

Additional information on mutation formats is found in: Sambrook et al., Molecular Cloning—A Laboratory Manual (3rd Ed.), Vol. 1-3, Cold Spring Harbor Laboratory, Cold Spring Harbor, N.Y., 2000 ("Sambrook"); Current Protocols in Molecular Biology, F. M. Ausubel et al., eds., Current Protocols, a joint venture between Greene Publishing Associates, Inc. and John Wiley & Sons, Inc., (supplemented through 2011) ("Ausubel")) and PCR Protocols A Guide to Methods and Applications (Innis et al. eds) Academic Press Inc. San Diego, Calif. (1990) ("Innis"). The following publications and references cited within provide additional detail on mutation formats: Arnold, Protein engineering for unusual environments, Current Opinion in Biotechnology 4:450-455 (1993); Bass et al., Mutant Trp repressors with new DNA-binding specificities, Science 242:240-245 (1988); Bordo and Argos (1991) Suggestions for "Safe" Residue Substitutions in Site-directed Mutagenesis 217:721-729; Botstein & Shortle, Strategies and applications of in vitro mutagenesis, Science 229:1193-1201 (1985); Carter et al., Improved oligonucleotide site-directed mutagenesis using M13 vectors, Nucl. Acids Res. 13: 4431-4443 (1985); Carter, Site-directed mutagenesis, Biochem. J. 237:1-7 (1986); Carter, Improved oligonucleotide-directed mutagenesis using M13 vectors, Methods in Enzymol. 154: 382-403 (1987); Dale et al., Oligonucleotide-directed random mutagenesis using the phosphorothioate method, Methods Mol. Biol. 57:369-374 (1996); Eghtedarzadeh & Henikoff, Use of oligonucleotides to generate large deletions, Nucl. Acids Res. 14: 5115 (1986); Fritz et al., Oligonucleotide-directed construction of mutations: a gapped duplex DNA procedure without enzymatic reactions in vitro, Nucl. Acids Res. 16: 6987-6999 (1988); Grundstrom et al., Oligonucleotide-directed mutagenesis by microscale shot-gun' gene synthesis, Nucl. Acids Res. 13: 3305-3316 (1985); Hayes (2002) Combining Computational and Experimental Screening for rapid Optimization of Protein Properties PNAS 99(25) 15926-15931; Kunkel, The efficiency of oligonucleotide directed mutagenesis, in Nucleic Acids & Molecular Biology (Eckstein, F. and Lilley, D. M. J. eds., Springer Verlag, Berlin)) (1987); Kunkel, Rapid and efficient site-specific mutagenesis without phenotypic selection, Proc. Natl. Acad. Sci. USA 82:488-492 (1985); Kunkel et al., Rapid and efficient site-specific mutagenesis without phenotypic selection, Methods in Enzymol. 154, 367-382 (1987); Kramer et al., The gapped duplex DNA approach to oligonucleotide-directed mutation construction, Nucl. Acids Res. 12: 9441-9456 (1984); Kramer & Fritz Oligonucleotide-directed construction of mutations via gapped duplex DNA, Methods in Enzymol. 154:350-367 (1987); Kramer et al., Point Mismatch Repair, Cell 38:879-887 (1984); Kramer et al., Improved enzymatic in vitro reactions in the gapped duplex DNA approach to oligonucleotide-directed construction of mutations, Nucl. Acids Res. 16: 7207 (1988); Ling et al., Approaches to DNA mutagenesis: an overview, Anal Biochem. 254(2): 157-178 (1997); Lorimer and Pastan Nucleic Acids Res. 23, 3067-8 (1995); Mandecki, Oligonucleotide-directed double-strand break repair in plasmids of Escherichia coli: a method for site-specific mutagenesis, Proc. Natl. Acad. Sci. USA, 83:7177-7181(1986); Nakamaye & Eckstein, Inhibition of restriction endonuclease Nci I cleavage by phosphorothioate groups and its application to oligonucleotide-directed mutagenesis, Nucl. Acids Res. 14: 9679-9698 (1986); Nambiar et al., Total synthesis and cloning of a gene coding for the ribonuclease S protein, Science 223: 1299-1301(1984); Sakamar and Khorana, Total synthesis and expression of a gene for the a-subunit of bovine rod outer segment guanine nucleotide-binding protein (transducin), Nucl. Acids Res. 14: 6361-6372 (1988); Sayers et al., Y-T Exonucleases in phosphorothioate-based oligonucleotide-directed mutagenesis, Nucl. Acids Res. 16:791-802 (1988); Sayers et al., Strand specific cleavage of phosphorothioate-containing DNA by reaction with restriction endonucleases in the presence of ethidium bromide, (1988) Nucl. Acids Res. 16: 803-814; Sieber, et al., Nature Biotechnology, 19:456-460 (2001); Smith, In vitro mutagenesis, Ann. Rev. Genet. 19:423-462 (1985); Methods in Enzymol. 100: 468-500 (1983); Methods in Enzymol. 154: 329-350 (1987); Stemmer, Nature 370, 389-91(1994); Taylor et al., The use of phosphorothioate-modified DNA in restriction enzyme reactions to prepare nicked DNA, Nucl. Acids Res. 13: 8749-8764 (1985); Taylor et al., The rapid generation of oligonucleotide-directed mutations at high frequency using phosphorothioate-modified DNA, Nucl. Acids Res. 13: 8765-8787 (1985); Wells et al., Importance of hydrogen-bond formation in stabilizing the transition state of subtilisin, Phil. Trans. R. Soc. Lond. A 317: 415-423 (1986); Wells et al., Cassette mutagenesis: an efficient method for generation of multiple mutations at defined sites, Gene 34:315-323 (1985); Zoller & Smith, Oligonucleotide-directed mutagenesis using M 13-derived vectors: an efficient and general procedure for the production of point mutations in any DNA fragment, Nucleic Acids Res. 10:6487-6500 (1982); Zoller & Smith, Oligonucleotide-directed mutagenesis of DNA fragments cloned into M13 vectors, Methods in Enzymol. 100:468-500 (1983); Zoller & Smith, Oligonucleotide-directed mutagenesis: a simple method using two oligonucleotide primers and a single-stranded DNA template, Methods in Enzymol. 154:329-350 (1987); Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296. Additional details on many of the above methods can be found in Methods in Enzymology Volume 154, which also describes useful controls for trouble-shooting problems with various mutagenesis methods.

Making and Isolating Recombinant Polymerases

Generally, nucleic acids encoding a polymerase as presented herein can be made by cloning, recombination, in vitro synthesis, in vitro amplification and/or other available methods. A variety of recombinant methods can be used for expressing an expression vector that encodes a polymerase as presented herein. Methods for making recombinant nucleic acids, expression and isolation of expressed products are well known and described in the art. A number of exemplary mutations and combinations of mutations, as well as strategies for design of desirable mutations, are described herein. Methods for making and selecting mutations in the active site of polymerases, including for modifying steric features in or near the active site to permit improved access by nucleotide analogs are found herein and, e.g., in WO 2007/076057 and WO 2008/051530.

Additional useful references for mutation, recombinant and in vitro nucleic acid manipulation methods (including cloning, expression, PCR, and the like) include Berger and Kimmel, Guide to Molecular Cloning Techniques, Methods in Enzymology volume 152 Academic Press, Inc., San Diego, Calif. (Berger); Kaufman et al. (2003) Handbook of Molecular and Cellular Methods in Biology and Medicine Second Edition Ceske (ed) CRC Press (Kaufman); The Nucleic Acid Protocols Handbook Ralph Rapley (ed) (2000) Cold Spring Harbor, Humana Press Inc (Rapley); Chen et al. (ed) PCR Cloning Protocols, Second Edition (Methods in Molecular Biology, volume 192) Humana Press; and in Viljoen et al. (2005) Molecular Diagnostic PCR Handbook Springer, ISBN 1402034032.

In addition, a plethora of kits are commercially available for the purification of plasmids or other relevant nucleic acids from cells, (see, e.g., EasyPrep™ and FlexiPrep™, both from Pharmacia Biotech; StrataClean™, from Stratagene; and QIAprep™ from Qiagen). Any isolated and/or purified nucleic acid can be further manipulated to produce other nucleic acids, used to transfect cells, incorporated into related vectors to infect organisms for expression, and/or the like. Typical cloning vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both.

Other useful references, e.g. for cell isolation and culture (e.g., for subsequent nucleic acid isolation) include Freshney (1994) Culture of Animal Cells, a Manual of Basic Technique, third edition, Wiley-Liss, New York and the references cited therein; Payne et al. (1992) Plant Cell and Tissue Culture in Liquid Systems John Wiley & Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York); and Atlas and Parks (eds) The Handbook of Microbiological Media (1993) CRC Press, Boca Raton, Fla.

The present disclosure also includes nucleic acids encoding the altered polymerases disclosed herein. A particular amino acid can be encoded by multiple codons, and certain translation systems (e.g., prokaryotic or eukaryotic cells) often exhibit codon bias, e.g., different organisms often prefer one of the several synonymous codons that encode the same amino acid. As such, nucleic acids presented herein are optionally "codon optimized," meaning that the nucleic acids are synthesized to include codons that are preferred by the particular translation system being employed to express the polymerase. For example, when it is desirable to express the polymerase in a bacterial cell (or even a particular strain of bacteria), the nucleic acid can be synthesized to include codons most frequently found in the genome of that bacterial cell, for efficient expression of the polymerase. A similar strategy can be employed when it is desirable to express the polymerase in a eukaryotic cell, e.g., the nucleic acid can include codons preferred by that eukaryotic cell.

A variety of protein isolation and detection methods are known and can be used to isolate polymerases, e.g., from recombinant cultures of cells expressing the recombinant polymerases presented herein. A variety of protein isolation and detection methods are well known in the art, including, e.g., those set forth in R. Scopes, Protein Purification, Springer-Verlag, N.Y. (1982); Deutscher, Methods in Enzymology Vol. 182: Guide to Protein Purification, Academic Press, Inc. N.Y. (1990); Sandana (1997) Bioseparation of Proteins, Academic Press, Inc.; Bollag et al. (1996) Protein Methods, 2nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3rd Edition Springer Verlag, NY; Janson and Ryden (1998) Protein Purification: Principles, High Resolution Methods and Applications, Second Edition Wiley-VCH, NY; and Walker (1998) Protein Protocols on CD-ROM Humana Press, NJ; and the references cited therein. Additional details regarding protein purification and detection methods can be found in Satinder Ahuja ed., Handbook of Bioseparations, Academic Press (2000).

Methods of Use

The altered polymerases presented herein can be used in a sequencing procedure, such as a sequencing-by-synthesis (SBS) technique. Briefly, SBS can be initiated by contacting the target nucleic acids with one or more nucleotides (e.g., labelled, synthetic, modified, or a combination thereof), DNA polymerase, etc. Those features where a primer is extended using the target nucleic acid as template will incorporate a labeled nucleotide that can be detected. The incorporation time used in a sequencing run can be significantly reduced using the altered polymerases described herein. Optionally, the labeled nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems, and detection platforms that can be readily adapted for use with an array produced by the methods of the present disclosure are described, for example, in Bentley et al., Nature 456: 53-59 (2008); WO 04/018497; WO 91/06678; WO 07/123744; U.S. Pat. Nos. 7,057,026, 7,329,492, 7,211,414, 7,315,019, 7,405,281, and 8,343,746.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568 and 6,274,320). In pyrosequencing, released PPi can be detected by being converted to adenosine triphosphate (ATP) by ATP sulfurylase, and the resulting ATP can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be used for application of pyrosequencing to arrays of the present disclosure are described, for example, in WO 2012/058096, US Pat. App. Pub. No. 2005/0191698 A1, U.S. Pat. Nos. 7,595,883 and 7,244,559.

Some embodiments can use methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides. Techniques and reagents for FRET-based sequencing are described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008).

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in U.S. Pat. Nos. 8,262,900, 7,948,015, 8,349,167, and US Published Patent Application No. 2010/0137143 A1.

Accordingly, presented herein are methods for incorporating nucleotide analogues into DNA including allowing the following components to interact: (i) an altered polymerase according to any of the above embodiments, (ii) a DNA template; and (iii) a nucleotide solution. In certain embodiments, the DNA template include a clustered array. In certain embodiments, the nucleotides are modified at the 3' sugar hydroxyl, and include modifications at the 3' sugar hydroxyl such that the substituent is larger in size than the naturally occurring 3' hydroxyl group.

Nucleic Acids Encoding Altered Polymerases

The present disclosure also includes nucleic acid molecules encoding the altered polymerases described herein. For any given altered polymerase which is a mutant version of a polymerase for which the amino acid sequence and preferably also the wild type nucleotide sequence encoding the polymerase is known, it is possible to obtain a nucleotide sequence encoding the mutant according to the basic principles of molecular biology. For example, given that the wild type nucleotide sequence encoding 9°N polymerase is known, it is possible to deduce a nucleotide sequence encoding any given mutant version of 9°N having one or more amino acid substitutions using the standard genetic code. Similarly, nucleotide sequences can readily be derived for mutant versions other polymerases such as, for example, Vent® polymerase, Deep Vent® polymerase, Pfu polymerase, KOD polymerase, Pab polymerase, etc. Nucleic acid molecules having the required nucleotide sequence may then be constructed using standard molecular biology techniques known in the art.

In accordance with the embodiments presented herein, a defined nucleic acid includes not only the identical nucleic acid but also any minor base variations including, in particular, substitutions in cases which result in a synonymous codon (a different codon specifying the same amino acid residue) due to the degenerate code in conservative amino acid substitutions. The term "nucleic acid sequence" also includes the complementary sequence to any single stranded sequence given regarding base variations.

The nucleic acid molecules described herein may also, advantageously, be included in a suitable expression vector to express the polymerase proteins encoded therefrom in a suitable host. Incorporation of cloned DNA into a suitable expression vector for subsequent transformation of said cell and subsequent selection of the transformed cells is well known to those skilled in the art as provided in Sambrook et al. (1989), Molecular cloning: A Laboratory Manual, Cold Spring Harbor Laboratory.

Such an expression vector includes a vector having a nucleic acid according to the embodiments presented herein operably linked to regulatory sequences, such as promoter regions, that are capable of effecting expression of said DNA fragments. The term "operably linked" refers to a juxtaposition wherein the components described are in a relationship permitting them to function in their intended manner. Such vectors may be transformed into a suitable host cell to provide for the expression of a protein according to the embodiments presented herein.

The nucleic acid molecule may encode a mature protein or a protein having a pro-sequence, including that encoding a leader sequence on the preprotein which is then cleaved by the host cell to form a mature protein. The vectors may be, for example, plasmid, virus or phage vectors provided with an origin of replication, and optionally a promoter for the expression of said nucleotide and optionally a regulator of the promoter. The vectors may contain one or more selectable markers, such as, for example, an antibiotic resistance gene.

Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. Such vectors may be obtained commercially or be assembled from the sequences described by methods well known in the art.

Transcription of DNA encoding the polymerase by higher eukaryotes may be optimized by including an enhancer sequence in the vector. Enhancers are cis-acting elements of DNA that act on a promoter to increase the level of transcription. Vectors will also generally include origins of replication in addition to the selectable markers.

The present disclosure also provides a kit for performing a nucleotide incorporation reaction. The kit includes at least one altered polymerase described herein and a nucleotide solution in a suitable packaging material in an amount sufficient for at least one nucleotide incorporation reaction. Optionally, other reagents such as buffers and solutions needed to use the altered polymerase and nucleotide solution are also included. Instructions for use of the packaged components are also typically included.

In certain embodiments, the nucleotide solution includes labelled nucleotides. In certain embodiments, the nucleotides are synthetic nucleotides. In certain embodiments, the nucleotides are modified nucleotides. In certain embodiments, a modified nucleotide has been modified at the 3' sugar hydroxyl such that the substituent is larger in size than the naturally occurring 3' hydroxyl group. In certain embodiments, the modified nucleotides include a modified nucleotide or nucleoside molecule that includes a purine or pyrimidine base and a ribose or deoxyribose sugar moiety having a removable 3'-OH blocking group covalently attached thereto, such that the 3' carbon atom has attached a group of the structure

—O—Z wherein Z is any of —C(R')$_2$—O—R", —C(R')$_2$—N(R")$_2$, —C(R')$_2$—N(H)R", —C(R')$_2$—S—R" and —C(R')$_2$—F, wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or (R')$_2$ represents an alkylidene group of formula =C(R''')$_2$ wherein each R''' may be the same or different and is selected from the group comprising hydrogen and halogen atoms and alkyl groups; and wherein the molecule may be reacted to yield an intermediate in which each R" is exchanged for H or, where Z is —C(R')$_2$—F, the F is exchanged for OH, SH or NH$_2$, preferably OH, which intermediate dissociates under aqueous conditions to afford a molecule with a free 3'OH;

with the proviso that where Z is —C(R')$_2$—S—R", both R' groups are not H.

In certain embodiments, R' of the modified nucleotide or nucleoside is an alkyl or substituted alkyl. In certain embodiments, —Z of the modified nucleotide or nucleoside is of formula —C(R')$_2$—N$_3$. In certain embodiments, Z is an azidomethyl group.

In certain embodiments, the modified nucleotides are fluorescently labelled to allow their detection. In certain embodiments, the modified nucleotides include a nucleotide or nucleoside having a base attached to a detectable label via a cleavable linker. In certain embodiments, the detectable label includes a fluorescent label.

As used herein, the phrase "packaging material" refers to one or more physical structures used to house the contents of the kit. The packaging material is constructed by known methods, preferably to provide a sterile, contaminant-free environment. The packaging material has a label which indicates that the components can be used for conducting a nucleotide incorporation reaction. In addition, the packaging material contains instructions indicating how the materials within the kit are employed to practice a nucleotide incorporation reaction. As used herein, the term "package" refers to a solid matrix or material such as glass, plastic, paper, foil, and the like, capable of holding within fixed limits the polypeptides. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed, and reference has been made to possible variations within the scope of this invention. These and other variations, combinations, and modifications in the invention will be apparent to those skilled in the art without departing from the scope of the invention, and it should be understood that

EXEMPLARY EMBODIMENTS

Embodiment 1

A recombinant DNA polymerase comprising an amino acid sequence that is at least 80% identical to a 9°N DNA polymerase amino acid sequence SEQ ID NO:1, wherein the DNA polymerase comprises an amino acid substitution mutation at a position functionally equivalent to Ala281, Phe283, Thr349, or Trp397 in the 9°N DNA polymerase amino acid sequence.

Embodiment 2

The polymerase of Embodiment 1, wherein the substitution mutation at the position functionally equivalent to Ala281 comprises a mutation to a non-polar, hydrophobic, or uncharged amino acid.

Embodiment 3

The polymerase of any one of Embodiments 1-2, wherein the substitution mutation at the position functionally equivalent to Ala281 comprises a mutation to Gly or Phe.

Embodiment 4

The polymerase of any one of Embodiments 1-3, wherein the substitution mutation at the position functionally equivalent to Phe283 comprises a mutation to a polar of uncharged amino acid.

Embodiment 5

The polymerase of any one of Embodiments 1-4, wherein the substitution mutation at the position functionally equivalent to Phe283 comprises a mutation to Ser.

Embodiment 6

The polymerase of any one of Embodiments 1-5, wherein the substitution mutation at the position functionally equivalent to Thr349 comprises a mutation to a polar or uncharged amino acid.

Embodiment 7

The polymerase of any one of Embodiments 1-6, wherein the substitution mutation at the position functionally equivalent to Thr349 comprises a mutation to Ser or Asn.

Embodiment 8

The polymerase of any one of Embodiments 1-7, wherein the substitution mutation at the position functionally equivalent to Thr349 comprises a mutation to a charged amino acid.

Embodiment 9

The polymerase of any one of Embodiments 1-8, wherein the substitution mutation at the position functionally equivalent to Thr349 comprises a mutation to Lys.

Embodiment 10

The polymerase of any one of Embodiments 1-9, wherein the substitution mutation at the position functionally equivalent to Trp397 comprises a mutation to a polar or uncharged amino acid.

Embodiment 11

The polymerase of any one of Embodiments 1-10, wherein the substitution mutation at the position functionally equivalent to Trp397 comprises a mutation to Cys.

Embodiment 12

The polymerase of any one of Embodiments 1-11, wherein the substitution mutation at the position functionally equivalent to Trp397 comprises a mutation to a non-polar or hydrophobic amino acid.

Embodiment 13

The polymerase of any one of Embodiments 1-12, wherein the substitution mutation at the position functionally equivalent to Trp397 comprises a mutation to Phe.

Embodiment 14

The polymerase of any one of Embodiments 1-13, wherein the polymerase comprises at least two, at least three, or four amino acid substitution mutations at positions functionally equivalent to an amino acid selected from A281, F283, Thr349, or Trp397 in the 9°N DNA polymerase amino acid sequence.

Embodiment 15

The polymerase of any one of Embodiments 1-14, wherein the polymerase comprises the substitution mutation at the position functionally equivalent to Thr349, and further comprises amino acid substitution mutations at positions functionally equivalent to amino acids Met129, Asp141, Glu143, Cys223, Leu408, Tyr409, Pro410, Ala485, Tyr497, Arg247, Glu599, and His633 in the 9°N DNA polymerase amino acid sequence.

Embodiment 16

The polymerase of any one of Embodiments 1-15, wherein the substitution mutation at the position functionally equivalent to Thr349 comprises a mutation to a charged amino acid.

Embodiment 17

The polymerase of any one of Embodiments 1-16, wherein the substitution mutation at the position functionally equivalent to Thr349 comprises a mutation to Lys.

Embodiment 18

The polymerase of any one of Embodiments 1-17, wherein the substitution mutation at the position functionally equivalent to Met129 comprises a mutation to a non-polar or hydrophobic amino acid.

Embodiment 19

The polymerase of any one of Embodiments 1-18, wherein the substitution mutation at the position functionally equivalent to Met129 comprises a mutation to Ala.

Embodiment 20

The polymerase of any one of Embodiments 1-19, wherein the substitution mutation at the position functionally equivalent to Asp141 comprises a mutation to a nonpolar or hydrophobic amino acid.

Embodiment 21

The polymerase of any one of Embodiments 1-20, wherein the substitution mutation at the position functionally equivalent to Asp141 comprises a mutation to Ala.

Embodiment 22

The polymerase of any one of Embodiments 1-21, wherein the substitution mutation at the position functionally equivalent to Glu143 comprises a mutation to a nonpolar or hydrophobic amino acid.

Embodiment 23

The polymerase of any one of Embodiments 1-22, wherein the substitution mutation at the position functionally equivalent to Glu143 comprises a mutation to Ala.

Embodiment 24

The polymerase of any one of Embodiments 1-23, wherein the substitution mutation at the position functionally equivalent to Cys223 comprises a mutation to a polar or uncharged amino acid.

Embodiment 25

The polymerase of any one of Embodiments 1-24, wherein the substitution mutation at the position functionally equivalent to Cys223 comprises a mutation to Ser.

Embodiment 26

The polymerase of any one of Embodiments 1-25, wherein the substitution mutation at the position functionally equivalent to Leu408 comprises a mutation to a nonpolar or hydrophobic amino acid.

Embodiment 27

The polymerase of any one of Embodiments 1-26, wherein the substitution mutation at the position functionally equivalent to Leu408 comprises a mutation to Ala.

Embodiment 28

The polymerase of any one of Embodiments 1-27, wherein the substitution mutation at the position functionally equivalent to Tyr409 comprises a mutation to a nonpolar or hydrophobic amino acid.

Embodiment 29

The polymerase of any one of Embodiments 1-28, wherein the substitution mutation at the position functionally equivalent to Tyr409 comprises a mutation to Ala.

Embodiment 30

The polymerase of any one of Embodiments 1-29, wherein the substitution mutation at the position functionally equivalent to Pro410 comprises a mutation to a nonpolar or hydrophobic amino acid.

Embodiment 31

The polymerase of any one of Embodiments 1-30, wherein the substitution mutation at the position functionally equivalent to Pro410 comprises a mutation to Ile.

Embodiment 32

The polymerase of any one of Embodiments 1-31, wherein the substitution mutation at the position functionally equivalent to Ala485 comprises a mutation to a nonpolar or hydrophobic amino acid.

Embodiment 33

The polymerase of any one of Embodiments 1-32, wherein the substitution mutation at the position functionally equivalent to Ala485 comprises a mutation to Val.

Embodiment 34

The polymerase of any one of Embodiments 1-33, wherein the substitution mutation at the position functionally equivalent to Tyr497 comprises a mutation to a nonpolar, hydrophobic, or uncharged amino acid.

Embodiment 35

The polymerase of any one of Embodiments 1-34, wherein the substitution mutation at the position functionally equivalent to Tyr497 comprises a mutation to Gly.

Embodiment 36

The polymerase of any one of Embodiments 1-35, wherein the substitution mutation at the position functionally equivalent to Arg247 comprises a mutation to a polar or uncharged amino acid.

Embodiment 37

The polymerase of any one of Embodiments 1-36, wherein the substitution mutation at the position functionally equivalent to Arg247 comprises a mutation to Tyr.

Embodiment 38

The polymerase of any one of Embodiments 1-37, wherein the substitution mutation at the position functionally equivalent to Glu599 comprises a mutation to a polar amino acid.

Embodiment 39

The polymerase of any one of Embodiments 1-38, wherein the substitution mutation at the position functionally equivalent to Glu599 comprises a mutation to Asp.

Embodiment 40

The polymerase of any one of Embodiments 1-39, wherein the substitution mutation at the position functionally equivalent to His633 comprises a mutation to a nonpolar, hydrophobic, or uncharged amino acid.

Embodiment 41

The polymerase of any one of Embodiments 1-40, wherein the substitution mutation at the position functionally equivalent to His633 comprises a mutation to Gly.

Embodiment 42

The polymerase of any one of Embodiments 1-41, further comprising an amino acid substitution mutation at a position functionally equivalent to Tyr497 and at least one amino acid substitution mutation at a position functionally equivalent to Arg247, Glu599, or His633 in the 9°N DNA polymerase amino acid sequence.

Embodiment 43

The polymerase of any one of Embodiments 1-42, wherein the substitution mutation at the position functionally equivalent to Tyr497 comprises a mutation to a nonpolar, hydrophobic, or uncharged amino acid.

Embodiment 44

The polymerase of any one of Embodiments 1-43, wherein the substitution mutation at the position functionally equivalent to Tyr497 comprises a mutation to Gly.

Embodiment 45

The polymerase of any one of Embodiments 1-44, wherein the substitution mutation at the position functionally equivalent to Arg247 comprises a mutation to a polar or uncharged amino acid.

Embodiment 46

The polymerase of any one of Embodiments 1-45, wherein the substitution mutation at the position functionally equivalent to Arg247 comprises a mutation to Tyr.

Embodiment 47

The polymerase of any one of Embodiments 1-46, wherein the substitution mutation at the position functionally equivalent to Glu599 comprises a mutation to a polar amino acid.

Embodiment 48

The polymerase of any one of Embodiments 1-47, wherein the substitution mutation at the position functionally equivalent to Glu599 comprises a mutation to Asp.

Embodiment 49

The polymerase of any one of Embodiments 1-48, wherein the substitution mutation at the position functionally equivalent to His633 comprises a mutation to a nonpolar, hydrophobic, or uncharged amino acid.

Embodiment 50

The polymerase of any one of Embodiments 1-49, wherein the substitution mutation at the position functionally equivalent to His633 comprises a mutation to Gly.

Embodiment 51

The polymerase of any one of Embodiments 1-50, wherein the polymerase comprises an amino acid substitution mutation at a position functionally equivalent to Tyr497 and at least two or three amino acid substitution mutations at positions functionally equivalent to an amino acid selected from Arg247, Glu599, or His633 in the 9°N DNA polymerase amino acid sequence.

Embodiment 52

The polymerase of any one of Embodiments 1-51, further comprising at least one amino acid substitution mutation at a position functionally equivalent to Lys620 or Val661 in the 9°N DNA polymerase amino acid sequence.

Embodiment 53

The polymerase of any one of Embodiments 1-52, wherein the substitution mutation at the position functionally equivalent to Lys620 comprises a mutation to a polar amino acid.

Embodiment 54

The polymerase of any one of Embodiments 1-53, wherein the substitution mutation at the position functionally equivalent to Lys620 comprises a mutation to Arg.

Embodiment 55

The polymerase of any one of Embodiments 1-53, wherein the substitution mutation at the position functionally equivalent to Val661 comprises a mutation to a polar amino acid.

Embodiment 56

The polymerase of any one of Embodiments 1-55, wherein the substitution mutation at the position functionally equivalent to Val661 comprises a mutation to Asp.

Embodiment 57

The polymerase of any one of Embodiments 1-56, wherein the polymerase comprises an amino acid substitution mutation at a position functionally equivalent to Tyr497 and at least two, at least three, at least four, or at least five amino acid substitution mutations at positions functionally equivalent to an amino acid selected from Arg247, Glu599, His633, Lys620, or Val661 in the 9°N DNA polymerase amino acid sequence.

Embodiment 58

The polymerase of any one of Embodiments 1-57, wherein the polymerase further comprises amino acid substitution mutations at positions functionally equivalent to amino acids Met129, Asp141, Glu143, Cys223, Leu408, Tyr409, Pro410, or Ala485 in the 9°N DNA polymerase amino acid sequence.

Embodiment 59

A recombinant DNA polymerase comprising an amino acid sequence that is at least 80% identical to a 9°N DNA polymerase amino acid sequence SEQ ID NO:8, wherein the DNA polymerase comprises an amino acid substitution mutation at a position functionally equivalent to Ala281Gly in the 9°N DNA polymerase amino acid sequence.

Embodiment 60

A recombinant DNA polymerase comprising an amino acid sequence that is at least 80% identical to a 9°N DNA polymerase amino acid sequence SEQ ID NO: 8, wherein the DNA polymerase comprises an amino acid substitution mutation at a position functionally equivalent to Ala281Phe in the 9°N DNA polymerase amino acid sequence.

Embodiment 61

A recombinant DNA polymerase comprising an amino acid sequence that is at least 80% identical to a 9°N DNA polymerase amino acid sequence SEQ ID NO: 8, wherein the DNA polymerase comprises an amino acid substitution mutation at a position functionally equivalent to Phe283 Ser in the 9°N DNA polymerase amino acid sequence.

Embodiment 62

A recombinant DNA polymerase comprising an amino acid sequence that is at least 80% identical to a 9°N DNA polymerase amino acid sequence SEQ ID NO: 8, wherein the DNA polymerase comprises an amino acid substitution mutation at a position functionally equivalent to Thr349Ser in the 9°N DNA polymerase amino acid sequence.

Embodiment 63

A recombinant DNA polymerase comprising an amino acid sequence that is at least 80% identical to a 9°N DNA polymerase amino acid sequence SEQ ID NO: 8, wherein the DNA polymerase comprises an amino acid substitution mutation at a position functionally equivalent to Thr349Asn in the 9°N DNA polymerase amino acid sequence.

Embodiment 64

A recombinant DNA polymerase comprising an amino acid sequence that is at least 80% identical to a 9°N DNA polymerase amino acid sequence SEQ ID NO: 8, wherein the DNA polymerase comprises an amino acid substitution mutation at a position functionally equivalent to Thr349Lys in the 9°N DNA polymerase amino acid sequence.

Embodiment 65

A recombinant DNA polymerase comprising an amino acid sequence that is at least 80% identical to a 9°N DNA polymerase amino acid sequence SEQ ID NO: 8, wherein the DNA polymerase comprises an amino acid substitution mutation at a position functionally equivalent to Trp397Cys in the 9°N DNA polymerase amino acid sequence.

Embodiment 66

A recombinant DNA polymerase comprising an amino acid sequence that is at least 80% identical to a 9°N DNA polymerase amino acid sequence SEQ ID NO: 8, wherein the DNA polymerase comprises an amino acid substitution mutation at a position functionally equivalent to Trp397Phe in the 9°N DNA polymerase amino acid sequence.

Embodiment 67

A recombinant DNA polymerase comprising an amino acid sequence that is at least 80% identical to a 9°N DNA polymerase amino acid sequence SEQ ID NO: 8, wherein the DNA polymerase comprises an amino acid substitution mutation at a position functionally equivalent to His633Thr in the 9°N DNA polymerase amino acid sequence.

Embodiment 68

A DNA polymerase comprising the amino acid sequence of any one of SEQ ID NOs:9-17.

Embodiment 69

The polymerase of any one of Embodiments 1-68, wherein the polymerase is a family B type DNA polymerase.

Embodiment 70

The polymerase of any one of Embodiments 1-69, wherein the polymerase is selected from the group consisting of a family B archaeal DNA polymerase, a human DNA polymerase-a, T4 polymerase, RB69 polymerase, and phi29 phage DNA polymerase.

Embodiment 71

The polymerase of any one of Embodiments 1-70, wherein the family B archaeal DNA polymerase is from a genus selected from the group consisting of *Thermococcus*, *Pyrococcus*, and *Methanococcus*.

Embodiment 72

The polymerase of any of any one of Embodiments 1-71, wherein the polymerase comprises reduced exonuclease activity as compared to a wild type polymerase.

Embodiment 73

A nucleic acid molecule encoding a polymerase as defined in any one of any one of Embodiments 1-72.

Embodiment 74

An expression vector comprising the nucleic acid molecule of Embodiment 73.

Embodiment 75

A host cell comprising the vector of Embodiment 74.

Embodiment 76

A method for incorporating modified nucleotides into DNA comprising allowing the following components to interact: (i) a polymerase according to any one of any one of Embodiments 1-72, (ii) a DNA template; and (iii) a nucleotide solution.

Embodiment 77

The method of Embodiment 76, wherein the DNA template comprises a clustered array.

Embodiment 78

A kit for performing a nucleotide incorporation reaction comprising: a polymerase as defined in any one of any one of Embodiments 1-72 and a nucleotide solution.

Embodiment 79

The kit of any one of Embodiment 78, wherein the nucleotide solution comprises labelled nucleotides.

Embodiment 80

The kit of any one of Embodiments 78-79, wherein the nucleotides comprise synthetic nucleotides.

Embodiment 81

The kit of any one of Embodiments 78-80, wherein the nucleotides comprise modified nucleotides.

Embodiment 82

The kit of any one of Embodiments 78-81, wherein the modified nucleotides have been modified at the 3' sugar hydroxyl such that the substituent is larger in size than the naturally occurring 3' hydroxyl group.

Embodiment 83

The kit of any one of Embodiments 78-82, wherein the modified nucleotides comprise a modified nucleotide or nucleoside molecule comprising a purine or pyrimidine base and a ribose or deoxyribose sugar moiety having a removable 3'-OH blocking group covalently attached thereto, such that the 3' carbon atom has attached a group of the structure

—O—Z wherein Z is any of —C(R')$_2$—O—R", —C(R)$_2$—N(R")$_2$, —C(R')$_2$—N(H)R", —C(R')$_2$—S—R" and —C(R')$_2$—F, wherein each R" is or is part of a removable protecting group;

each R' is independently a hydrogen atom, an alkyl, substituted alkyl, arylalkyl, alkenyl, alkynyl, aryl, heteroaryl, heterocyclic, acyl, cyano, alkoxy, aryloxy, heteroaryloxy or amido group, or a detectable label attached through a linking group; or (R')$_2$ represents an alkylidene group of formula =C(R''')$_2$ wherein each R''' may be the same or different and is selected from the group comprising hydrogen and halogen atoms and alkyl groups; and wherein said molecule may be reacted to yield an intermediate in which each R" is exchanged for H or, where Z is —C(R')$_2$—F, the F is exchanged for OH, SH or NH$_2$, preferably OH, which intermediate dissociates under aqueous conditions to afford a molecule with a free 3'OH;

with the proviso that where Z is —C(R')$_2$—S—R", both R' groups are not H.

Embodiment 84

The kit of any one of Embodiments 78-83, wherein R' of the modified nucleotide or nucleoside is an alkyl or substituted alkyl.

Embodiment 85

The kit of any one of Embodiments 78-84, wherein —Z of the modified nucleotide or nucleoside is of formula —C(R)$_2$—N$_3$.

Embodiment 86

The kit of any one of Embodiments 78-85, wherein Z is an azidomethyl group.

87. The kit of any one of Embodiments 78-86, wherein the modified nucleotides are fluorescently labelled to allow their detection.

88. The kit of any one of Embodiments 78-86, wherein the modified nucleotides comprise a nucleotide or nucleoside having a base attached to a detectable label via a cleavable linker.

89. The kit of any one of Embodiments 78-88, wherein the detectable label comprises a fluorescent label.

90. The kit of any one of Embodiments 78-88, further comprising one or more DNA template molecules and/or primers.

EXAMPLES

The present invention is illustrated by the following examples. It is to be understood that the particular examples, materials, amounts, and procedures are to be interpreted broadly in accordance with the scope and spirit of the invention as set forth herein.

Example 1

General Assay Methods and Conditions

Unless otherwise noted, this describes the general assay conditions used in the Examples described herein.

A. Cloning and Expression of Polymerases

Methods for making recombinant nucleic acids, expression, and isolation of expressed products are known and described in the art. Mutagenesis was performed on the coding region encoding a 9°N polymerase (SEQ ID NO:1) using standard site-directed mutagenesis methodology. PCR-based approaches were used to amplify mutated coding regions and add a His-tag. For each mutation made, the proper sequence of the altered coding region was confirmed by determining the sequence of the cloned DNA.

His-tagged mutant polymerase coding regions were subcloned into pET11a vector and transformed into BL21 Star (DE3) expression cells (Invitrogen). Overnight cultures from single-picked colonies were used to inoculate expression cultures in 2.8 L flasks. Cultures were grown at 37° C. until OD600 of about 0.8, protein expression was then induced with 0.2 mM IPTG and followed by 4 hours of additional growth. Cultures were centrifuged at 7000 rpm for 20 minutes. Cell pellets were stored at −20° C. until purification.

Pellets were freeze-thawed and lysed with 5× w/v lysis buffer (50 mM Tris-HCl pH7.5, 1 mM EDTA, 0.1% BME, and 5% Glycerol) in the presence of Ready-Lyse and Omnicleave reagents (Epicentre) according to manufacturer recommendations. The final NaCl concentration was raised to 500 mM and lysate was incubated on ice for 5 minutes. Following centrifugation, the supernatant was incubated at 80° C. for about 70 minutes. All further purification was performed at 4° C. Supernatant was iced for 30 min before being centrifuged and purified using 5 mL Ni Sepharose HP columns (GE). Columns were pre-equilibrated with Buffer A (50 mM Tris-HCl pH 7.5, 1 mM EDTA, 5% Glycerol, 500 mM NaCl, and 20 mM Imidazole). The column was eluted using a 75 mL gradient from 20 to 500 mM imidazole. Peak fractions were pooled and diluted with 10% glycerol to match the conductivity of SP Buffer A (50 mM Tris-HCl pH 7.5, 150 mM NaCl, 1 mM EDTA, 5% Glycerol) and loaded onto 5 mL SP Sepharose columns (GE). The column was eluted using a 100 mL gradient from 150 to 1000 mM NaCl. Peak fractions were pooled, dialyzed into storage buffer (10 mM Tris-HCl pH 7.5, 300 mM KCL, 0.1 mM EDTA, and 50% Glycerol) and stored at −20° C.

B. Error Rate and Phasing Analysis

Sequencing experiments were used to compare error rates and phasing values. Unless indicated otherwise, the experiments were carried out on a MiniSeq™ system (Illumina, Inc., San Diego, Calif.), according to manufacturer instructions. For example, for each polymerase, a separate incorporation mix (IMX) was prepared and used in a short run (35 cycles in read 1) or long run (227 cycle run of 151 in read 1 and 76 in read 2). Standard MiniSeq Mid Output Reagent Cartridge formulations were used, with the standard polymerase substituted with the polymerase being tested, at a concentration of 90 µg/mL. The time for incubation of IMX on the flowcell varied as noted in the Examples herein. The DNA library used was made following the standard TruSeq™ Nano protocol (Illumina, Inc.), with 350 bp target insert size, using E. coli genomic DNA; PhiX DNA (Illumina, Inc) was added to resulting library in ~1:10 molar ratio. Illumina RTA Software was used to evaluate error rate on both genomes as well as phasing levels.

Example 2

Sequencing Performance of Selected Altered Polymerases

A number of altered polymerases were identified that had error rates and phasing levels in a short run under a short incorporation time (e.g., 16 sec) that were not significantly greater than a control polymerase used in a short run under a standard incorporation time (46 sec). The quality metrics used to evaluate the altered polymerases were the phasing rates ("Read1 Phasing") and cumulative error rates of E. coli and bacteriophage PhiX sequencing controls ("Read1 Error"). The quality metrics were compared to corresponding Pol 1671 and Pol 812 phasing and error rates at the standard incorporation time during long sequencing runs (227 cycles of 151 in read 1 and 76 in read 2). Results are summarized in FIG. 2.

FIG. 2 shows the error rates and phasing levels of selected altered polymerases of the present disclosure. Starting at the bottom of the figure, "slow" refers to slow incorporation time, i.e., the standard incorporation time of 46 seconds; "fast" refers to the faster incorporation time of 16 seconds; "1671", "1901", etc., identify specific altered polymerases; WT, T349K, T349N, T349S, etc., refer to specific mutations in an altered polymerase relative to Pol 1671 ("WT" corresponds to Pol 1671 for the purposes of this application); and Pols 1671 and e812 refer to control polymerases.

A number of newly identified mutants, e.g., Pols 1895, 1901, 1920, 1962, 1980, 2089, 2098, and 2139, demonstrated lower error rates under a short incorporation time than the Pol 1671 control without a significant increase in phasing. Notably, Pols 1901 and 1920 showed both lower phasing and cumulative error rates relative to the Pol 1671 standard. These altered polymerases are characterized by substitutions at position 349, wherein a threonine is replaced with a lysine (Pol 1901) or asparagine (Pol 1920).

Example 3

Superior Sequencing Performance of Pol 1901

To identify the limits of polymerase performance, two different lots of Pol 1671 were compared to Pol 1901 at different incorporation speeds throughout a series of 35-cycle sequencing runs. The quality metrics used to compare the altered polymerases were the cumulative error rate, phasing, pre-phasing, and % Q30. Pol 812 was once again used as a standard. Results are summarized in FIG. 3.

Figure 3:
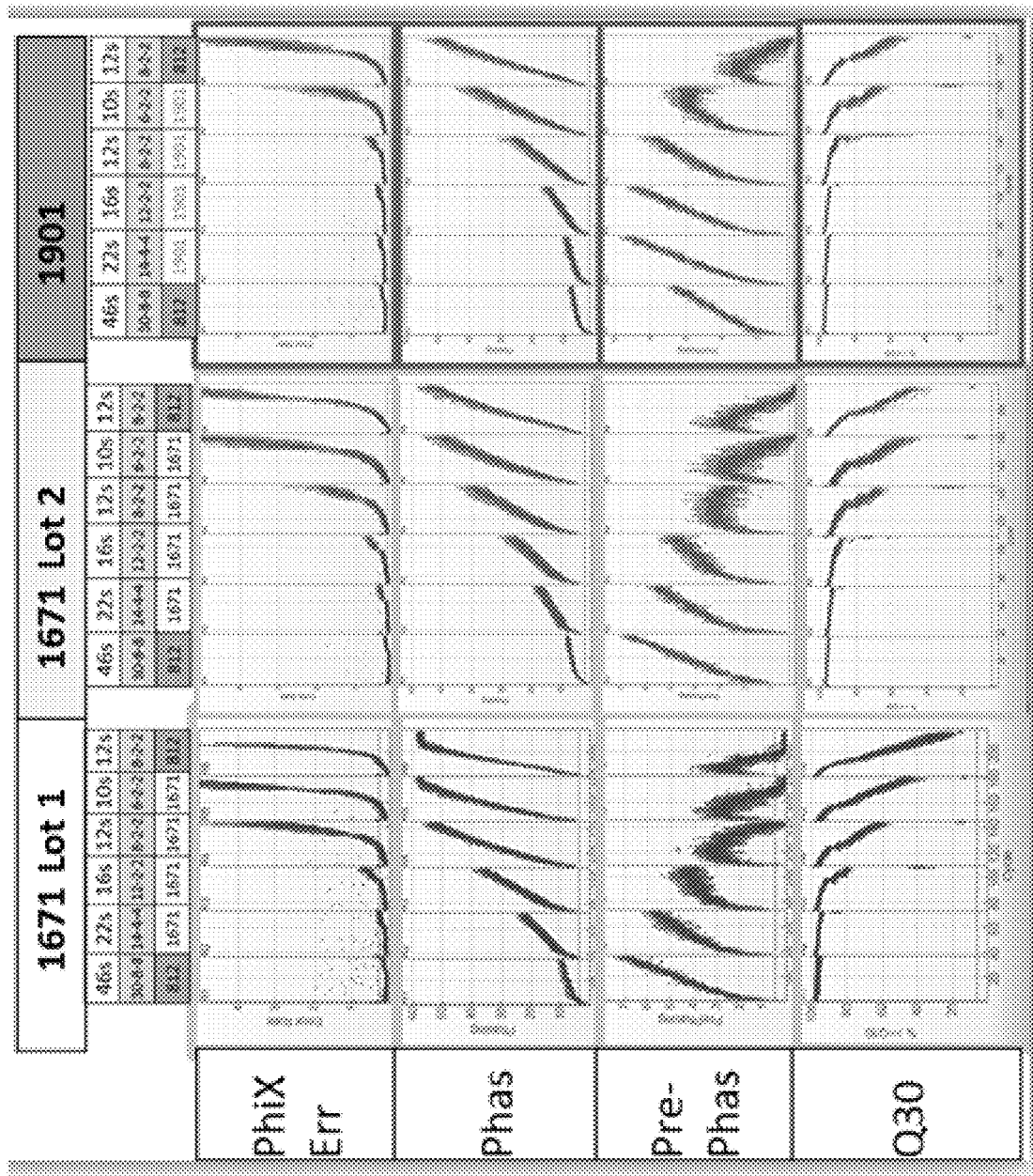
FIG. 3 compares various error metrics of polymerases 1671 (two different lots) and 1901 at different incorporation speeds. Polymerase 812 was used as a control. In the first row, "46s", "22s", "16s", "12s", and "10s" refer to the total incorporation time. In the second row, "30-8-8", "14-4-4", etc. refer to the static incubation period (in seconds) followed by the two mixing periods (also in seconds). The third row refers to the identities of the altered polymerases. On the Y axis, "PhiX Err" refers to the observed error rates; "Phas" refers to the observed phasing values; "Pre-Phas" refers to the observed pre-phasing values; and "Q30" refers to the percentage of reads that pass the Q30 quality filter, i.e. an error rate of less of equal to 1 in 1000, or 0.1%.

In the first row of FIG. 3, "46s", "22s", "16s", "12s", and "10s" refer to the total incorporation time. In the second row, "30-8-8", "14-4-4", etc. refer to the static incubation period (in seconds) followed by the two mixing periods (also in seconds). The third row refers to the identities of the altered polymerases. "PhiX Err" refers to the observed error rates; "Phas" refers to the observed phasing values; "Pre-Phas" refers to the observed pre-phasing values; and "Q30" refers to the percentage of reads that pass the Q30 quality filter, i.e. an error rate of less of equal to 1 in 1000, or 0.1%.

Referring to the PhiX error rates, FIG. 3 shows that Pol 1901 maintained a low error rate at as low as 12 sec total incorporation time, whereas the Pol 1671 error rate increased dramatically below 16 sec incorporation time. Similar improvements in Pol 1901 over Pol 1671 were observed at 12 sec total incorporation time in the phasing, pre-phasing and % Q30 sequencing quality metrics.

The complete disclosure of all patents, patent applications (whether published or not), and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Any patent, patent application (whether published or not), or other literature referred to herein in hereby incorporated herein in its respective entirety or in part to the extent that it does not conflict with the disclosure presented herein.

In addition to the documents already cited in this application, reference is hereby made to provisional U.S. Patent Application No. 62/753,558, identically entitled "Polymerases, compositions, and methods of use," filed Oct. 31, 2018. The entire contents of this application is also incorporated herein by reference.

The invention claimed is:

1. A recombinant altered DNA polymerase comprising an amino acid sequence that is at least 80% identical to the 9°N DNA polymerase amino acid sequence comprising SEQ ID NO:1, wherein the DNA polymerase comprises at least one amino acid substitution mutation at a position functionally equivalent to Ala281, Phe283, Thr349, or Trp397 in the 9°N DNA polymerase amino acid sequence.

2. The polymerase of claim 1, wherein the substitution mutation at the position functionally equivalent to Ala281 comprises a mutation to a non-polar, hydrophobic, or uncharged amino acid.

3. The polymerase of claim 2, wherein the substitution mutation at the position functionally equivalent to Ala281 comprises a mutation to Gly or Phe.

4. The polymerase of claim 1, wherein the substitution mutation at the position functionally equivalent to Phe283 comprises a mutation to a polar or uncharged amino acid.

5. The polymerase of claim 4, wherein the substitution mutation at the position functionally equivalent to Phe283 comprises a mutation to Ser.

6. The polymerase of claim 1, wherein the substitution mutation at the position functionally equivalent to Thr349 comprises a mutation to a polar or uncharged amino acid.

7. The polymerase of claim 6, wherein the substitution mutation at the position functionally equivalent to Thr349 comprises a mutation to Ser or Asn.

8. The polymerase of claim 1, wherein the substitution mutation at the position functionally equivalent to Thr349 comprises a mutation to a charged amino acid.

9. The polymerase of claim 8, wherein the substitution mutation at the position functionally equivalent to Thr349 comprises a mutation to Lys.

10. The polymerase of claim 1, wherein the substitution mutation at the position functionally equivalent to Trp397 comprises a mutation to a polar or uncharged amino acid.

11. The polymerase of claim 10, wherein the substitution mutation at the position functionally equivalent to Trp397 comprises a mutation to Cys.

12. The polymerase of claim 1, wherein the substitution mutation at the position functionally equivalent to Trp397 comprises a mutation to a non-polar or hydrophobic amino acid.

13. The polymerase of claim 10, wherein the substitution mutation at the position functionally equivalent to Trp397 comprises a mutation to Phe.

14. The polymerase of claim 1, wherein the polymerase comprises at least two, at least three, or four amino acid substitution mutations at positions functionally equivalent to an amino acid selected from A281, F283, Thr349, or Trp397 in the 9°N DNA polymerase amino acid sequence.

15. The polymerase of claim 1, wherein the polymerase comprises the substitution mutation at the position functionally equivalent to Thr349, and further comprises amino acid substitution mutations at positions functionally equivalent to amino acids Met129, Asp141, Glu143, Cys223, Leu408, Tyr409, Pro410, Ala485, Tyr497, Arg247, Glu599, and His633 in the 9°N DNA polymerase amino acid sequence.

16. The polymerase of claim 15, wherein the substitution mutation at the position functionally equivalent to Thr349 comprises a mutation to a charged amino acid.

17. The polymerase of claim 16, wherein the substitution mutation at the position functionally equivalent to Thr349 comprises a mutation to Lys.

18. The polymerase of claim 15, wherein the substitution mutation at the position functionally equivalent to Met129 comprises a mutation to Ala.

19. The polymerase of claim 15, wherein the substitution mutation at the position functionally equivalent to Asp141 comprises a mutation to Ala.

20. The polymerase of claim 15, wherein the substitution mutation at the position functionally equivalent to Glu143 comprises a mutation to Ala.

21. The polymerase of claim 15, wherein the substitution mutation at the position functionally equivalent to Cys223 comprises a mutation to Ser.

22. The polymerase of claim 15, wherein the substitution mutation at the position functionally equivalent to Leu408 comprises a mutation to Ala.

23. The polymerase of claim 15, wherein the substitution mutation at the position functionally equivalent to Tyr409 comprises a mutation to Ala.

24. The polymerase of claim 15, wherein the substitution mutation at the position functionally equivalent to Pro410 comprises a mutation to Ile.

25. The polymerase of claim 15, wherein the substitution mutation at the position functionally equivalent to Ala485 comprises a mutation to Val.

26. The polymerase of claim 15, wherein the substitution mutation at the position functionally equivalent to Tyr497 comprises a mutation to Gly.

27. The polymerase of claim 15, wherein the substitution mutation at the position functionally equivalent to Arg247 comprises a mutation to Tyr.

28. The polymerase of claim 15, wherein the substitution mutation at the position functionally equivalent to Glu599 comprises a mutation to Asp.

29. The polymerase of claim 15, wherein the substitution mutation at the position functionally equivalent to His633 comprises a mutation to Gly.

30. A DNA polymerase comprising the amino acid sequence of any one of SEQ ID NOs:9-17.

* * * * *

SEQUENCE LISTING

```
<160> NUMBER OF SEQ ID NOS: 17

<210> SEQ ID NO 1
<211> LENGTH: 775
<212> TYPE: PRT
<213> ORGANISM: artificial
<220> FEATURE:
<223> OTHER INFORMATION: Engineered Polymerase

<400> SEQUENCE: 1

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Thr Met Leu Ala Phe Asp Ile Glu Thr
        130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255
```

```
His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
        290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670
```

```
Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
        755                 760                 765

Leu Lys Val Lys Gly Lys Lys
    770                 775

<210> SEQ ID NO 2
<211> LENGTH: 774
<212> TYPE: PRT
<213> ORGANISM: artificial
<220> FEATURE:
<223> OTHER INFORMATION: Engineered Polymerase

<400> SEQUENCE: 2

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Ala Ile Ala Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255
```

```
Arg Ile His Phe Asp Leu Phe Pro Val Val Arg Thr Ile Asn Leu
                260                 265                 270
Pro Thr Tyr Thr Leu Glu Ala Val Tyr Glu Ala Val Leu Gly Lys Thr
            275                 280                 285
Lys Ser Lys Leu Gly Ala Glu Glu Ile Ala Ala Ile Trp Glu Thr Glu
        290                 295                 300
Glu Ser Met Lys Lys Leu Ala Gln Tyr Ser Met Glu Asp Ala Arg Ala
305                 310                 315                 320
Thr Tyr Glu Leu Gly Lys Glu Phe Phe Pro Met Glu Ala Glu Leu Ala
                325                 330                 335
Lys Leu Ile Gly Gln Ser Val Trp Asp Val Ser Arg Ser Ser Thr Gly
            340                 345                 350
Asn Leu Val Glu Trp Tyr Leu Leu Arg Val Ala Tyr Ala Arg Asn Glu
        355                 360                 365
Leu Ala Pro Asn Lys Pro Asp Glu Glu Tyr Lys Arg Arg Leu Arg
    370                 375                 380
Thr Thr Tyr Leu Gly Gly Tyr Val Lys Glu Pro Glu Lys Gly Leu Trp
385                 390                 395                 400
Glu Asn Ile Ile Tyr Leu Asp Phe Arg Ser Leu Tyr Pro Ser Ile Ile
                405                 410                 415
Val Thr His Asn Val Ser Pro Asp Thr Leu Glu Lys Glu Gly Cys Lys
            420                 425                 430
Asn Tyr Asp Val Ala Pro Ile Val Gly Tyr Arg Phe Cys Lys Asp Phe
        435                 440                 445
Pro Gly Phe Ile Pro Ser Ile Leu Gly Asp Leu Ile Ala Met Arg Gln
    450                 455                 460
Asp Ile Lys Lys Met Lys Ser Thr Ile Asp Pro Ile Glu Lys Lys
465                 470                 475                 480
Met Leu Asp Tyr Arg Gln Arg Ala Ile Lys Leu Leu Ala Asn Ser Tyr
                485                 490                 495
Tyr Gly Tyr Met Gly Tyr Pro Lys Ala Arg Trp Tyr Ser Lys Glu Cys
            500                 505                 510
Ala Glu Ser Val Thr Ala Trp Gly Arg His Tyr Ile Glu Met Thr Ile
        515                 520                 525
Arg Glu Ile Glu Glu Lys Phe Gly Phe Lys Val Leu Tyr Ala Asp Thr
    530                 535                 540
Asp Gly Phe Tyr Ala Thr Ile Pro Gly Glu Lys Pro Glu Leu Ile Lys
545                 550                 555                 560
Lys Lys Ala Lys Glu Phe Leu Asn Tyr Ile Asn Ser Lys Leu Pro Gly
                565                 570                 575
Leu Leu Glu Leu Glu Tyr Glu Gly Phe Tyr Leu Arg Gly Phe Phe Val
            580                 585                 590
Thr Lys Lys Arg Tyr Ala Val Ile Asp Glu Glu Gly Arg Ile Thr Thr
        595                 600                 605
Arg Gly Leu Glu Val Val Arg Arg Asp Trp Ser Glu Ile Ala Lys Glu
    610                 615                 620
Thr Gln Ala Lys Val Leu Glu Ala Ile Leu Lys Glu Gly Ser Val Glu
625                 630                 635                 640
Lys Ala Val Glu Val Val Arg Asp Val Val Glu Lys Ile Ala Lys Tyr
                645                 650                 655
Arg Val Pro Leu Glu Lys Leu Val Ile His Glu Gln Ile Thr Arg Asp
            660                 665                 670
Leu Lys Asp Tyr Lys Ala Ile Gly Pro His Val Ala Ile Ala Lys Arg
```

```
                   675                 680                 685
Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Tyr Tyr Ile
                    725                 730                 735

Glu Asn Gln Val Leu Pro Ala Val Leu Arg Ile Leu Glu Ala Phe Gly
                740                 745                 750

Tyr Arg Lys Glu Asp Leu Arg Tyr Gln Ser Ser Lys Gln Thr Gly Leu
            755                 760                 765

Asp Ala Trp Leu Lys Arg
770

<210> SEQ ID NO 3
<211> LENGTH: 777
<212> TYPE: PRT
<213> ORGANISM: artificial
<220> FEATURE:
<223> OTHER INFORMATION: Engineered Polymerase

<400> SEQUENCE: 3

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Val Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
```

```
            260                 265                 270
Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
        290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Tyr Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
        370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
                420                 425                 430

Asp Val Ala Pro Glu Val Gly His Lys Phe Cys Lys Asp Phe Pro Gly
            435                 440                 445

Phe Ile Pro Ser Leu Leu Lys Arg Leu Leu Asp Glu Arg Gln Glu Ile
        450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Glu Tyr Ile Glu Phe Val Arg Lys Glu
            515                 520                 525

Leu Glu Glu Lys Phe Gly Phe Lys Val Leu Tyr Ile Asp Thr Asp Gly
        530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
                580                 585                 590

Lys Lys Tyr Ala Leu Ile Asp Glu Glu Gly Lys Ile Ile Thr Arg Gly
            595                 600                 605

Leu Glu Ile Val Arg Arg Asp Trp Ser Glu Ile Ala Lys Glu Thr Gln
        610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
                660                 665                 670

Glu Tyr Lys Ala Ile Gly Pro His Val Ala Val Ala Lys Arg Leu Ala
            675                 680                 685
```

```
Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
                740                 745                 750

Lys Glu Asp Leu Arg Trp Gln Lys Thr Lys Gln Thr Gly Leu Thr Ala
                755                 760                 765

Trp Leu Asn Ile Lys Lys Lys Gly Ser
770                 775
```

<210> SEQ ID NO 4
<211> LENGTH: 775
<212> TYPE: PRT
<213> ORGANISM: artificial
<220> FEATURE:
<223> OTHER INFORMATION: Engineered Polymerase

<400> SEQUENCE: 4

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
                20                  25                  30

Thr Phe Arg Pro Tyr Ile Tyr Ala Leu Leu Arg Asp Asp Ser Lys Ile
            35                  40                  45

Glu Glu Val Lys Lys Ile Thr Gly Glu Arg His Gly Lys Ile Val Arg
50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
                100                 105                 110

Asp Ile Pro Phe Ala Lys Arg Tyr Leu Ile Asp Lys Gly Leu Ile Pro
            115                 120                 125

Met Glu Gly Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
                180                 185                 190

Arg Phe Leu Arg Ile Ile Arg Glu Lys Asp Pro Asp Ile Ile Val Thr
            195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
                260                 265                 270
```

```
Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
                340                 345                 350

Val Glu Trp Phe Leu Leu Arg Lys Ala Tyr Glu Arg Asn Glu Val Ala
            355                 360                 365

Pro Asn Lys Pro Ser Glu Glu Glu Tyr Gln Arg Arg Leu Arg Glu Ser
        370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
                500                 505                 510

Ser Val Thr Ala Trp Gly Arg Lys Tyr Ile Glu Leu Val Trp Lys Glu
    515                 520                 525

Leu Glu Glu Lys Phe Gly Phe Lys Val Leu Tyr Ile Asp Thr Asp Gly
        530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685
```

Ala Lys Gly Val Lys Ile Lys Pro Gly Met Val Ile Gly Tyr Ile Val
    690             695             700

Leu Arg Gly Asp Gly Pro Ile Ser Asn Arg Ala Ile Leu Ala Glu Glu
705             710             715             720

Tyr Asp Pro Lys His Lys Tyr Asp Ala Glu Tyr Tyr Ile Glu Asn
            725             730             735

Gln Val Leu Pro Ala Val Leu Arg Ile Leu Glu Gly Phe Gly Tyr Arg
            740             745             750

Lys Glu Asp Leu Arg Tyr Gln Lys Thr Arg Gln Val Gly Leu Thr Ser
            755             760             765

Trp Leu Asn Ile Lys Lys Ser
770             775

<210> SEQ ID NO 5
<211> LENGTH: 774
<212> TYPE: PRT
<213> ORGANISM: artificial
<220> FEATURE:
<223> OTHER INFORMATION: Engineered Polymerase

<400> SEQUENCE: 5

Met Ile Leu Asp Thr Asp Tyr Ile Thr Glu Asp Gly Lys Pro Val Ile
1               5               10              15

Arg Ile Phe Lys Lys Glu Asn Gly Glu Phe Lys Ile Glu Tyr Asp Arg
            20              25              30

Thr Phe Glu Pro Tyr Phe Tyr Ala Leu Leu Lys Asp Asp Ser Ala Ile
            35              40              45

Glu Glu Val Lys Lys Ile Thr Ala Glu Arg His Gly Thr Val Val Thr
50              55              60

Val Lys Arg Val Glu Lys Val Gln Lys Lys Phe Leu Gly Arg Pro Val
65              70              75              80

Glu Val Trp Lys Leu Tyr Phe Thr His Pro Gln Asp Val Pro Ala Ile
            85              90              95

Arg Asp Lys Ile Arg Glu His Pro Ala Val Ile Asp Ile Tyr Glu Tyr
            100             105             110

Asp Ile Pro Phe Ala Lys Arg Tyr Leu Ile Asp Lys Gly Leu Val Pro
            115             120             125

Met Glu Gly Asp Glu Glu Leu Lys Met Leu Ala Phe Ala Ile Ala Thr
130             135             140

Leu Tyr His Glu Gly Glu Glu Phe Ala Glu Gly Pro Ile Leu Met Ile
145             150             155             160

Ser Tyr Ala Asp Glu Glu Gly Ala Arg Val Ile Thr Trp Lys Asn Val
            165             170             175

Asp Leu Pro Tyr Val Asp Val Val Ser Thr Glu Arg Glu Met Ile Lys
            180             185             190

Arg Phe Leu Arg Val Val Lys Glu Lys Asp Pro Asp Val Leu Ile Thr
            195             200             205

Tyr Asn Gly Asp Asn Phe Asp Phe Ala Tyr Leu Lys Lys Arg Cys Glu
            210             215             220

Lys Leu Gly Ile Asn Phe Ala Leu Gly Arg Asp Gly Ser Glu Pro Lys
225             230             235             240

Ile Gln Arg Met Gly Asp Arg Phe Ala Val Glu Val Lys Gly Arg Ile
            245             250             255

His Phe Asp Leu Tyr Pro Val Ile Arg Arg Thr Ile Asn Leu Pro Thr
            260             265             270

-continued

```
Tyr Thr Leu Glu Ala Val Tyr Glu Ala Val Phe Gly Gln Pro Lys Glu
            275                 280                 285
Lys Val Tyr Ala Glu Glu Ile Thr Thr Ala Trp Glu Thr Gly Glu Asn
290                 295                 300
Leu Glu Arg Val Ala Arg Tyr Ser Met Glu Asp Ala Lys Val Thr Tyr
305                 310                 315                 320
Glu Leu Gly Lys Glu Phe Leu Pro Met Glu Ala Gln Leu Ser Arg Leu
                325                 330                 335
Ile Gly Gln Ser Leu Trp Asp Val Ser Arg Ser Ser Thr Gly Asn Leu
            340                 345                 350
Val Glu Trp Phe Leu Leu Arg Lys Ala Tyr Glu Arg Asn Glu Leu Ala
        355                 360                 365
Pro Asn Lys Pro Asp Glu Lys Glu Leu Ala Arg Arg Arg Gln Ser Tyr
    370                 375                 380
Glu Gly Gly Tyr Val Lys Glu Pro Glu Arg Gly Leu Trp Glu Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
            420                 425                 430
Val Ala Pro Gln Val Gly His Arg Phe Cys Lys Asp Phe Pro Gly Phe
        435                 440                 445
Ile Pro Ser Leu Leu Gly Asp Leu Leu Glu Glu Arg Gln Lys Ile Lys
    450                 455                 460
Lys Lys Met Lys Ala Thr Ile Asp Pro Ile Glu Arg Lys Leu Leu Asp
465                 470                 475                 480
Tyr Arg Gln Arg Ala Ile Lys Ile Leu Ala Asn Ser Tyr Tyr Gly Tyr
                485                 490                 495
Tyr Gly Tyr Ala Arg Ala Arg Trp Tyr Cys Lys Glu Cys Ala Glu Ser
            500                 505                 510
Val Thr Ala Trp Gly Arg Glu Tyr Ile Thr Met Thr Ile Lys Glu Ile
        515                 520                 525
Glu Glu Lys Tyr Gly Phe Lys Val Ile Tyr Ser Asp Thr Asp Gly Phe
    530                 535                 540
Phe Ala Thr Ile Pro Gly Ala Asp Ala Glu Thr Val Lys Lys Lys Ala
545                 550                 555                 560
Met Glu Phe Leu Lys Tyr Ile Asn Ala Lys Leu Pro Gly Ala Leu Glu
                565                 570                 575
Leu Glu Tyr Glu Gly Phe Tyr Lys Arg Gly Phe Phe Val Thr Lys Lys
            580                 585                 590
Lys Tyr Ala Val Ile Asp Glu Glu Gly Lys Ile Thr Thr Arg Gly Leu
        595                 600                 605
Glu Ile Val Arg Arg Asp Trp Ser Glu Ile Ala Lys Glu Thr Gln Ala
    610                 615                 620
Arg Val Leu Glu Ala Leu Leu Lys Asp Gly Asp Val Glu Lys Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Lys Asp
            660                 665                 670
Tyr Lys Ala Thr Gly Pro His Val Ala Val Ala Lys Arg Leu Ala Ala
        675                 680                 685
Arg Gly Val Lys Ile Arg Pro Gly Thr Val Ile Ser Tyr Ile Val Leu
```

-continued

```
            690                 695                 700
Lys Gly Ser Gly Arg Ile Gly Asp Arg Ala Ile Pro Phe Asp Glu Phe
705                     710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Ser Ala Trp
            755                 760                 765

Leu Lys Pro Lys Gly Thr
            770

<210> SEQ ID NO 6
<211> LENGTH: 773
<212> TYPE: PRT
<213> ORGANISM: artificial
<220> FEATURE:
<223> OTHER INFORMATION: Engineered Polymerase

<400> SEQUENCE: 6

Met Ile Ile Asp Ala Asp Tyr Ile Thr Glu Asp Gly Lys Pro Ile Ile
1               5                   10                  15

Arg Ile Phe Lys Lys Glu Lys Gly Glu Phe Lys Val Glu Tyr Asp Arg
            20                  25                  30

Thr Phe Arg Pro Tyr Ile Tyr Ala Leu Leu Lys Asp Asp Ser Ala Ile
        35                  40                  45

Asp Glu Val Lys Lys Ile Thr Ala Glu Arg His Gly Lys Ile Val Arg
    50                  55                  60

Ile Thr Glu Val Glu Lys Val Gln Lys Lys Phe Leu Gly Arg Pro Ile
65                  70                  75                  80

Glu Val Trp Lys Leu Tyr Leu Glu His Pro Gln Asp Val Pro Ala Ile
                85                  90                  95

Arg Glu Lys Ile Arg Glu His Pro Ala Val Val Asp Ile Phe Glu Tyr
            100                 105                 110

Asp Ile Pro Phe Ala Lys Arg Tyr Leu Ile Asp Lys Gly Leu Thr Pro
        115                 120                 125

Met Glu Gly Asn Glu Glu Leu Thr Phe Leu Ala Val Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Glu Gly Ala Lys Val Ile Thr Trp Lys Ser Ile
                165                 170                 175

Asp Leu Pro Tyr Val Glu Val Val Ser Ser Glu Arg Glu Met Ile Lys
            180                 185                 190

Arg Leu Val Lys Val Ile Arg Glu Lys Asp Pro Asp Val Ile Ile Thr
        195                 200                 205

Tyr Asn Gly Asp Asn Phe Asp Phe Pro Tyr Leu Leu Lys Arg Ala Glu
    210                 215                 220

Lys Leu Gly Ile Lys Leu Pro Leu Gly Arg Asp Asn Ser Glu Pro Lys
225                 230                 235                 240

Met Gln Arg Met Gly Asp Ser Leu Ala Val Glu Ile Lys Gly Arg Ile
                245                 250                 255

His Phe Asp Leu Phe Pro Val Ile Arg Arg Thr Ile Asn Leu Pro Thr
            260                 265                 270

Tyr Thr Leu Glu Ala Val Tyr Glu Ala Ile Phe Gly Lys Ser Lys Glu
```

```
                275                 280                 285
Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Phe
305                 310                 315                 320

Glu Leu Gly Lys Glu Phe Phe Pro Met Glu Ala Gln Leu Ala Arg Leu
                325                 330                 335

Val Gly Gln Pro Val Trp Asp Val Ser Arg Ser Thr Gly Asn Leu
            340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Tyr Glu Arg Arg Leu Arg Glu Ser
    370                 375                 380

Tyr Glu Gly Gly Tyr Val Lys Glu Pro Glu Lys Gly Leu Trp Glu Gly
385                 390                 395                 400

Ile Val Ser Leu Asp Phe Arg Ser Leu Tyr Pro Ser Ile Ile Ile Thr
                405                 410                 415

His Asn Val Ser Pro Asp Thr Leu Asn Arg Glu Asn Cys Lys Glu Tyr
            420                 425                 430

Asp Val Ala Pro Gln Val Gly His Arg Phe Cys Lys Asp Phe Pro Gly
            435                 440                 445

Phe Ile Pro Ser Leu Leu Gly Asn Leu Leu Glu Glu Arg Gln Lys Ile
450                 455                 460

Lys Lys Arg Met Lys Glu Ser Lys Asp Pro Val Glu Lys Lys Leu Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Gln Tyr Ile Asp Leu Val Arg Arg Glu
            515                 520                 525

Leu Glu Ser Arg Gly Phe Lys Val Leu Tyr Ile Asp Thr Asp Gly Leu
    530                 535                 540

Tyr Ala Thr Ile Pro Gly Ala Lys His Glu Glu Ile Lys Glu Lys Ala
545                 550                 555                 560

Leu Lys Phe Val Glu Tyr Ile Asn Ser Lys Leu Pro Gly Leu Leu Glu
                565                 570                 575

Leu Glu Tyr Glu Gly Phe Tyr Ala Arg Gly Phe Phe Val Thr Lys Lys
            580                 585                 590

Lys Tyr Ala Leu Ile Asp Glu Glu Gly Lys Ile Val Thr Arg Gly Leu
            595                 600                 605

Glu Ile Val Arg Arg Asp Trp Ser Glu Ile Ala Lys Glu Thr Gln Ala
    610                 615                 620

Lys Val Leu Glu Ala Ile Leu Lys His Gly Asn Val Asp Glu Ala Val
625                 630                 635                 640

Lys Ile Val Lys Glu Val Thr Glu Lys Leu Ser Lys Tyr Glu Ile Pro
                645                 650                 655

Pro Glu Lys Leu Val Ile Tyr Glu Gln Ile Thr Arg Pro Leu Ser Glu
            660                 665                 670

Tyr Lys Ala Ile Gly Pro His Val Ala Val Ala Lys Arg Leu Ala Ala
            675                 680                 685

Lys Gly Val Lys Val Lys Pro Gly Met Val Ile Gly Tyr Ile Val Leu
690                 695                 700
```

```
Arg Gly Asp Gly Pro Ile Ser Lys Arg Ala Ile Ala Ile Glu Glu Phe
705                 710                 715                 720

Asp Pro Lys Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Lys Tyr Gln Lys Thr Lys Gln Val Gly Leu Gly Ala Trp
        755                 760                 765

Leu Lys Phe Gly Ser
        770

<210> SEQ ID NO 7
<211> LENGTH: 775
<212> TYPE: PRT
<213> ORGANISM: artificial
<220> FEATURE:
<223> OTHER INFORMATION: Engineered Polymerase

<400> SEQUENCE: 7

Met Ile Leu Asp Ala Asp Tyr Ile Thr Glu Asp Gly Lys Pro Val Ile
1               5                   10                  15

Arg Val Phe Lys Lys Glu Lys Gly Glu Phe Lys Ile Asn Tyr Asp Arg
            20                  25                  30

Asp Phe Glu Pro Tyr Ile Tyr Ala Leu Leu Lys Asp Asp Ser Ala Ile
        35                  40                  45

Glu Asp Ile Lys Lys Ile Thr Ala Glu Arg His Gly Thr Thr Val Arg
    50                  55                  60

Val Thr Arg Ala Glu Arg Val Lys Lys Lys Phe Leu Gly Arg Pro Val
65                  70                  75                  80

Glu Val Trp Lys Leu Tyr Phe Thr His Pro Gln Asp Val Pro Ala Ile
                85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asn Glu Glu Leu Arg Met Leu Ala Phe Asp Ile Glu Thr
    130                 135                 140

Leu Tyr His Glu Gly Glu Glu Phe Gly Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Glu Ser Val Ser Thr Glu Lys Glu Met Ile Lys
            180                 185                 190

Arg Phe Leu Lys Val Ile Gln Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Thr Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Thr Val Tyr Glu Ala Ile Phe Gly Gln Pro Lys Glu
        275                 280                 285
```

```
Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Ala Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Ala Glu Ser Tyr
    370                 375                 380

Ala Gly Gly Tyr Val Lys Glu Pro Glu Lys Gly Leu Trp Glu Asn Ile
385                 390                 395                 400

Val Tyr Leu Asp Tyr Lys Ser Leu Tyr Pro Ser Ile Ile Ile Thr His
                405                 410                 415

Asn Val Ser Pro Asp Thr Leu Asn Arg Glu Gly Cys Arg Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Val Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Asn Ala Arg Trp Tyr Cys Arg Glu Cys Ala Glu Ser
            500                 505                 510

Val Thr Ala Trp Gly Arg Gln Tyr Ile Glu Thr Thr Met Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Thr
545                 550                 555                 560

Lys Glu Phe Leu Asn Tyr Ile Asn Pro Arg Leu Pro Gly Leu Leu Glu
                565                 570                 575

Leu Glu Tyr Glu Gly Phe Tyr Arg Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Arg Tyr Glu Val Pro
                645                 650                 655

Pro Glu Lys Leu Val Ile Tyr Glu Gln Ile Thr Arg Asn Leu Arg Asp
            660                 665                 670

Tyr Arg Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700
```

```
Lys Gly Pro Gly Arg Val Gly Asp Arg Ala Ile Pro Phe Asp Glu Phe
705                 710                 715                 720

Asp Pro Ala Lys His Arg Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Lys Gln Ala Gly Leu Gly Ala Trp
            755                 760                 765

Leu Lys Pro Lys Thr Gly Ser
            770         775

<210> SEQ ID NO 8
<211> LENGTH: 775
<212> TYPE: PRT
<213> ORGANISM: artificial
<220> FEATURE:
<223> OTHER INFORMATION: Engineered Polymerase

<400> SEQUENCE: 8

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
            85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
            165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285
```

```
Lys Val Tyr Ala Glu Glu Ile Ala Gln Ala Trp Glu Ser Gly Glu Gly
290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
        355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
        595                 600                 605

Glu Ile Val Arg Arg Asp Trp Ser Glu Ile Ala Lys Glu Thr Gln Ala
610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
```

```
                  705                 710                 715                 720
Asp Pro Thr Lys His Arg Tyr Asp Ala Glu Tyr Tyr Ile Glu Asn Gln
                  725                 730                 735

Val Leu Pro Ala Val Glu Arg Ile Leu Lys Ala Phe Gly Tyr Arg Lys
                  740                 745                 750

Glu Asp Leu Arg Tyr Gln Lys Thr Lys Gln Val Gly Leu Gly Ala Trp
                  755                 760                 765

Leu Lys Val Lys Gly Lys Lys
                  770                 775

<210> SEQ ID NO 9
<211> LENGTH: 775
<212> TYPE: PRT
<213> ORGANISM: artificial
<220> FEATURE:
<223> OTHER INFORMATION: Engineered Polymerase

<400> SEQUENCE: 9

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
                20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
        50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
                100                 105                 110

Asp Ile Pro Phe Ala Lys Arg Tyr Leu Ile Asp Lys Gly Leu Ile Pro
            115                 120                 125

Ala Glu Gly Asp Glu Glu Leu Thr Met Leu Ala Phe Ala Ile Ala Thr
        130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
                180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
        210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
                260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
```

```
            290                 295                 300
Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                    325                 330                 335

Ile Gly Gln Ser Leu Trp Asp Val Ser Arg Ser Ser Ser Gly Asn Leu
                340                 345                 350

Val Glu Trp Phe Leu Leu Arg Lys Ala Tyr Lys Arg Asn Glu Leu Ala
                355                 360                 365

Pro Asn Lys Pro Asp Glu Arg Glu Leu Ala Arg Arg Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                    405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
                435                 440                 445

Ile Pro Ser Leu Leu Gly Asp Leu Leu Glu Glu Arg Gln Lys Ile Lys
                450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                    485                 490                 495

Gly Gly Tyr Ala Lys Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
                515                 520                 525

Glu Glu Lys Phe Gly Phe Lys Val Leu Tyr Ala Asp Thr Asp Gly Leu
                530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                    565                 570                 575

Leu Glu Tyr Glu Gly Phe Tyr Val Arg Gly Phe Phe Val Thr Lys Lys
                580                 585                 590

Lys Tyr Ala Val Ile Asp Asp Glu Gly Lys Ile Thr Thr Arg Gly Leu
                595                 600                 605

Glu Ile Val Arg Arg Asp Trp Ser Glu Ile Ala Lys Glu Thr Gln Ala
610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                    645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
                690                 695                 700

Lys Gly Ser Gly Arg Ile Gly Asp Arg Ala Ile Pro Ala Asp Glu Phe
705                 710                 715                 720
```

```
Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
        740                 745                 750

Glu Asp Leu Arg Tyr Gln Lys Thr Lys Gln Val Gly Leu Gly Ala Trp
        755                 760                 765

Leu Lys Val Lys Gly Lys Lys
        770                 775

<210> SEQ ID NO 10
<211> LENGTH: 775
<212> TYPE: PRT
<213> ORGANISM: artificial
<220> FEATURE:
<223> OTHER INFORMATION: Engineered Polymerase

<400> SEQUENCE: 10

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300
```

```
Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Lys Gly Asn Leu
                340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
                595                 600                 605

Glu Ile Val Arg Arg Asp Trp Ser Glu Ile Ala Lys Glu Thr Gln Ala
            610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720
```

```
Asp Pro Thr Lys His Arg Tyr Asp Ala Glu Tyr Tyr Ile Glu Asn Gln
            725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 11
<211> LENGTH: 775
<212> TYPE: PRT
<213> ORGANISM: artificial
<220> FEATURE:
<223> OTHER INFORMATION: Engineered Polymerase

<400> SEQUENCE: 11

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
            35                  40                  45

Glu Asp Val Lys Lys Val Thr Ala Lys Arg His Gly Thr Val Val Lys
50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
            85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Ala Glu Gly Asp Glu Glu Leu Thr Met Leu Ala Phe Ala Ile Ala Thr
            130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
            165                 170                 175

Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
            210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
            275                 280                 285

Lys Val Tyr Ala Glu Glu Ile Ala Gln Ala Trp Glu Ser Gly Glu Gly
            290                 295                 300
```

```
Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Ser Asn Gly Asn Leu
                340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
```

```
                        725                 730                 735
Val Leu Pro Ala Val Glu Arg Ile Leu Lys Ala Phe Gly Tyr Arg Lys
                740                 745                 750

Glu Asp Leu Arg Tyr Gln Lys Thr Lys Gln Val Gly Leu Gly Ala Trp
            755                 760                 765

Leu Lys Val Lys Gly Lys Lys
770                 775

<210> SEQ ID NO 12
<211> LENGTH: 775
<212> TYPE: PRT
<213> ORGANISM: artificial
<220> FEATURE:
<223> OTHER INFORMATION: Engineered Polymerase

<400> SEQUENCE: 12

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Gly Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
```

```
            305                 310                 315                 320
Glu Leu Gly Arg Glu Phe Phe Pro Met Glu Ala Gln Leu Ser Arg Leu
                325                 330                 335

Ile Gly Gln Ser Leu Trp Asp Val Ser Arg Ser Thr Gly Asn Leu
                340                 345                 350

Val Glu Trp Phe Leu Leu Arg Lys Ala Tyr Lys Arg Asn Glu Leu Ala
                355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
                435                 440                 445

Ile Pro Ser Leu Leu Gly Asp Leu Leu Glu Glu Arg Gln Lys Ile Lys
                450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
                515                 520                 525

Glu Glu Lys Phe Gly Phe Lys Val Leu Tyr Ala Asp Thr Asp Gly Leu
                530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
                580                 585                 590

Lys Tyr Ala Val Ile Asp Asp Glu Gly Lys Ile Thr Thr Arg Gly Leu
                595                 600                 605

Glu Ile Val Arg Arg Asp Trp Ser Glu Ile Ala Lys Glu Thr Gln Ala
                610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
                660                 665                 670

Tyr Lys Ala Thr Gly Pro His Val Ala Val Ala Lys Arg Leu Ala Ala
                675                 680                 685

Arg Gly Val Lys Ile Arg Pro Gly Thr Val Ile Ser Tyr Ile Val Leu
                690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735
```

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
            755                 760                 765

Leu Lys Val Lys Gly Lys Lys
            770                 775

<210> SEQ ID NO 13
<211> LENGTH: 775
<212> TYPE: PRT
<213> ORGANISM: artificial
<220> FEATURE:
<223> OTHER INFORMATION: Engineered Polymerase

<400> SEQUENCE: 13

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Phe Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

```
Glu Leu Gly Arg Glu Phe Pro Met Glu Ala Gln Leu Ser Arg Leu
            325                 330                 335

Ile Gly Gln Ser Leu Trp Asp Val Ser Arg Ser Ser Thr Gly Asn Leu
        340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Thr His
            405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
    450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
            595                 600                 605

Glu Ile Val Arg Arg Asp Trp Ser Glu Ile Ala Lys Glu Thr Gln Ala
    610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735
```

```
Val Leu Pro Ala Val Glu Arg Ile Leu Lys Ala Phe Gly Tyr Arg Lys
                740                 745                 750

Glu Asp Leu Arg Tyr Gln Lys Thr Lys Gln Val Gly Leu Gly Ala Trp
            755                 760                 765

Leu Lys Val Lys Gly Lys Lys
        770                 775

<210> SEQ ID NO 14
<211> LENGTH: 775
<212> TYPE: PRT
<213> ORGANISM: artificial
<220> FEATURE:
<223> OTHER INFORMATION: Engineered Polymerase

<400> SEQUENCE: 14

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320
```

```
Glu Leu Gly Arg Glu Phe Phe Pro Met Glu Ala Gln Leu Ser Arg Leu
            325                 330                 335

Ile Gly Gln Ser Leu Trp Asp Val Ser Arg Ser Thr Gly Asn Leu
        340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Ala Ala Ile Ser Ile Ile Ile Thr His
                405                 410                 415

Asn Val Ser Pro Asp Thr Leu Asn Arg Glu Gly Cys Lys Glu Tyr Asp
                420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
        595                 600                 605

Glu Ile Val Arg Arg Asp Trp Ser Glu Ile Ala Lys Glu Thr Gln Ala
        610                 615                 620

Arg Val Leu Glu Ala Ile Leu Lys Thr Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
        690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
```

```
                    740                 745                 750
Glu Asp Leu Arg Tyr Gln Lys Thr Lys Gln Val Gly Leu Gly Ala Trp
            755                 760                 765

Leu Lys Val Lys Gly Lys Lys
        770                 775

<210> SEQ ID NO 15
<211> LENGTH: 775
<212> TYPE: PRT
<213> ORGANISM: artificial
<220> FEATURE:
<223> OTHER INFORMATION: Engineered Polymerase

<400> SEQUENCE: 15

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Ser Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
```

```
            325                 330                 335
Ile Gly Gln Ser Leu Trp Asp Val Ser Arg Ser Thr Gly Asn Leu
            340                 345                 350
Val Glu Trp Phe Leu Leu Arg Lys Ala Tyr Lys Arg Asn Glu Leu Ala
            355                 360                 365
Pro Asn Lys Pro Asp Glu Arg Glu Leu Ala Arg Arg Gly Gly Tyr
            370                 375                 380
Ala Gly Gly Tyr Val Lys Glu Pro Arg Gly Leu Trp Asp Asn Ile
385                 390                 395                 400
Val Tyr Leu Asp Phe Arg Ser Ala Ala Ile Ser Ile Ile Thr His
            405                 410                 415
Asn Val Ser Pro Asp Thr Leu Asn Arg Glu Gly Cys Lys Glu Tyr Asp
            420                 425                 430
Val Ala Pro Glu Val Gly His Lys Phe Cys Lys Asp Phe Pro Gly Phe
            435                 440                 445
Ile Pro Ser Leu Leu Gly Asp Leu Leu Glu Glu Arg Gln Lys Ile Lys
            450                 455                 460
Arg Lys Met Lys Ala Thr Val Asp Pro Leu Glu Lys Lys Leu Leu Asp
465                 470                 475                 480
Tyr Arg Gln Arg Val Ile Lys Ile Leu Ala Asn Ser Phe Tyr Gly Tyr
            485                 490                 495
Gly Gly Tyr Ala Lys Ala Arg Trp Tyr Cys Lys Glu Cys Ala Glu Ser
            500                 505                 510
Val Thr Ala Trp Gly Arg Glu Tyr Ile Glu Met Val Ile Arg Glu Leu
            515                 520                 525
Glu Glu Lys Phe Gly Phe Lys Val Leu Tyr Ala Asp Thr Asp Gly Leu
            530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
            565                 570                 575
Leu Glu Tyr Glu Gly Phe Tyr Val Arg Gly Phe Phe Val Thr Lys Lys
            580                 585                 590
Lys Tyr Ala Val Ile Asp Asp Glu Gly Lys Ile Thr Thr Arg Gly Leu
            595                 600                 605
Glu Ile Val Arg Arg Asp Trp Ser Glu Ile Ala Lys Glu Thr Gln Ala
            610                 615                 620
Arg Val Leu Glu Ala Ile Leu Lys Gly Gly Asp Val Glu Glu Ala Val
625                 630                 635                 640
Arg Ile Val Lys Glu Val Thr Glu Lys Leu Ser Lys Tyr Glu Val Pro
            645                 650                 655
Pro Glu Lys Leu Val Ile His Glu Gln Ile Thr Arg Asp Leu Arg Asp
            660                 665                 670
Tyr Lys Ala Thr Gly Pro His Val Ala Val Ala Lys Arg Leu Ala Ala
            675                 680                 685
Arg Gly Val Lys Ile Arg Pro Gly Thr Val Ile Ser Tyr Ile Val Leu
            690                 695                 700
Lys Gly Ser Gly Arg Ile Gly Asp Arg Ala Ile Pro Ala Asp Glu Phe
705                 710                 715                 720
Asp Pro Thr Lys His Arg Tyr Asp Ala Glu Tyr Tyr Ile Glu Asn Gln
            725                 730                 735
Val Leu Pro Ala Val Glu Arg Ile Leu Lys Ala Phe Gly Tyr Arg Lys
            740                 745                 750
```

```
Glu Asp Leu Arg Tyr Gln Lys Thr Lys Gln Val Gly Leu Gly Ala Trp
        755                 760                 765

Leu Lys Val Lys Gly Lys Lys
        770                 775

<210> SEQ ID NO 16
<211> LENGTH: 775
<212> TYPE: PRT
<213> ORGANISM: artificial
<220> FEATURE:
<223> OTHER INFORMATION: Engineered Polymerase

<400> SEQUENCE: 16

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335
```

```
Ile Gly Gln Ser Leu Trp Asp Val Ser Arg Ser Thr Gly Asn Leu
            340                 345                 350

Val Glu Trp Phe Leu Leu Arg Lys Ala Tyr Lys Arg Asn Glu Leu Ala
                355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Cys Asp Asn Ile
385                 390                 395                 400

Val Tyr Leu Asp Phe Arg Ser Ala Ala Ile Ser Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
            595                 600                 605

Glu Ile Val Arg Arg Asp Trp Ser Glu Ile Ala Lys Glu Thr Gln Ala
        610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
        690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750
```

```
Glu Asp Leu Arg Tyr Gln Lys Thr Lys Gln Val Gly Leu Gly Ala Trp
            755                 760                 765
Leu Lys Val Lys Gly Lys Lys
        770                 775
```

<210> SEQ ID NO 17
<211> LENGTH: 775
<212> TYPE: PRT
<213> ORGANISM: artificial
<220> FEATURE:
<223> OTHER INFORMATION: Engineered Polymerase

<400> SEQUENCE: 17

```
Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
            85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Ala Glu Gly Asp Glu Glu Leu Thr Met Leu Ala Phe Ala Ile Ala Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
            165                 170                 175

Asp Leu Pro Tyr Val Asp Val Ser Thr Glu Lys Glu Met Ile Lys
            180                 185                 190

Arg Phe Leu Arg Val Val Arg Glu Lys Asp Pro Asp Val Leu Ile Thr
            195                 200                 205

Tyr Asn Gly Asp Asn Phe Asp Phe Ala Tyr Leu Lys Lys Arg Ser Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Tyr Phe Ala Val Glu Val Lys Gly Arg Ile
            245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Gln Ala Trp Glu Ser Gly Glu Gly
    290                 295                 300

Leu Glu Arg Val Ala Arg Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
            325                 330                 335
```

```
Ile Gly Gln Ser Leu Trp Asp Val Ser Arg Ser Ser Thr Gly Asn Leu
            340                 345                 350

Val Glu Trp Phe Leu Leu Arg Lys Ala Tyr Lys Arg Asn Glu Leu Ala
            355                 360                 365

Pro Asn Lys Pro Asp Glu Arg Glu Leu Ala Arg Arg Gly Gly Tyr
        370                 375                 380

Ala Gly Gly Tyr Val Lys Glu Pro Glu Arg Gly Leu Phe Asp Asn Ile
385                 390                 395                 400

Val Tyr Leu Asp Phe Arg Ser Ala Ala Ile Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Glu Val Gly His Lys Phe Cys Lys Asp Phe Pro Gly Phe
            435                 440                 445

Ile Pro Ser Leu Leu Gly Asp Leu Leu Glu Glu Arg Gln Lys Ile Lys
        450                 455                 460

Arg Lys Met Lys Ala Thr Val Asp Pro Leu Glu Lys Lys Leu Leu Asp
465                 470                 475                 480

Tyr Arg Gln Arg Val Ile Lys Ile Leu Ala Asn Ser Phe Tyr Gly Tyr
                485                 490                 495

Gly Gly Tyr Ala Lys Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
            530                 535                 540

His Ala Thr Ile Pro Gly Ala Asp Ala Glu Thr Val Lys Lys Lys Ala
545                 550                 555                 560

Lys Glu Phe Leu Lys Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Asp Glu Gly Lys Ile Thr Thr Arg Gly Leu
            595                 600                 605

Glu Ile Val Arg Arg Asp Trp Ser Glu Ile Ala Lys Glu Thr Gln Ala
610                 615                 620

Arg Val Leu Glu Ala Ile Leu Lys Gly Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Arg Asp
            660                 665                 670

Tyr Lys Ala Thr Gly Pro His Val Ala Val Ala Lys Arg Leu Ala Ala
            675                 680                 685

Arg Gly Val Lys Ile Arg Pro Gly Thr Val Ile Ser Tyr Ile Val Leu
            690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
            740                 745                 750

Glu Asp Leu Arg Tyr Gln Lys Thr Lys Gln Val Gly Leu Gly Ala Trp
```

|  |  |  |
|---|---|---|
| 755 | 760 | 765 |
| Leu Lys Val Lys Gly Lys Lys | | |
| 770 | 775 | |